United States Patent
Ito

(10) Patent No.: US 9,365,619 B2
(45) Date of Patent: Jun. 14, 2016

(54) IGG-BINDING PEPTIDE AND METHOD FOR DETECTING AND PURIFYING IGG USING SAME

(75) Inventor: Yuji Ito, Kagoshima (JP)

(73) Assignees: Otsuka Chemical Co., Ltd., Osaka (JP); Kagoshima University, Kagoshima (JP)

( * ) Notice: Subject to any disclaimer, the term of this patent is extended or adjusted under 35 U.S.C. 154(b) by 46 days.

(21) Appl. No.: 14/240,083

(22) PCT Filed: Aug. 23, 2012

(86) PCT No.: PCT/JP2012/071303
§ 371 (c)(1),
(2), (4) Date: Apr. 28, 2014

(87) PCT Pub. No.: WO2013/027796
PCT Pub. Date: Feb. 28, 2013

(65) Prior Publication Data
US 2014/0274790 A1 Sep. 18, 2014

(30) Foreign Application Priority Data
Aug. 24, 2011 (JP) ................................ 2011-182539

(51) Int. Cl.
| C07K 7/08 | (2006.01) |
| G01N 33/68 | (2006.01) |
| C07K 17/00 | (2006.01) |
| C07K 1/22 | (2006.01) |
| C07K 17/06 | (2006.01) |
| G01N 30/88 | (2006.01) |

(52) U.S. Cl.
CPC ... *C07K 7/08* (2013.01); *C07K 1/22* (2013.01); *C07K 17/00* (2013.01); *C07K 17/06* (2013.01); *G01N 33/6854* (2013.01); *C07K 2319/00* (2013.01); *G01N 2030/8831* (2013.01)

(58) Field of Classification Search
CPC ............ C07K 7/08; C07K 1/22; C07K 17/00; C07K 17/06; C07K 2319/00; G01N 33/6854; G01N 2030/8831
See application file for complete search history.

(56) References Cited

U.S. PATENT DOCUMENTS

| 2004/0087765 A1 | 5/2004 | Ronspeck et al. |
| 2010/0297606 A1 | 11/2010 | Ito et al. |

FOREIGN PATENT DOCUMENTS

| WO | WO 01/45746 A2 | 6/2001 |
| WO | WO 02/38592 A2 | 5/2002 |
| WO | WO 02/086070 A2 | 10/2002 |
| WO | WO 2005/086947 A2 | 9/2005 |
| WO | WO 2008/054030 A1 | 5/2008 |

OTHER PUBLICATIONS

Sakamoto et al. "Discovery and Characterization of a Peptide Motif That Specifically Recognizes a Non-native Conformation of Human IgG Induced by Acidic pH Conditions" The Journal of Biological Chemistry vol. 284, No. 15, pp. 9986-9993, Apr. 10, 2009.*
Supplementary European Search Report dated Jan. 20, 2015, in EP 12825488.5.
DeLano et al., "Convergent Solutions to Binding at a Protein-Protein Interface," Science, Feb. 18, 2000, 287(5456):1279-1283.
Jung et al., "Controlled antibody immobilization onto immunoanalytical platforms by synthetic peptide," Analytical Biochemistry, 2008, available online Oct. 23, 2007, 374(1):99-105.
Strambio-de-Castillia et al., "A Method for the Rapid and Efficient Elution of Native Affinity-Purified Protein a Tagged Complexes," Journal of Proteome Research, Dec. 1, 2005, 4(6):2250-2256.
Verkhivker et al., "Monte Carlo Simulations of the Peptide Recognition at the Consensus Binding Site of the Constant Fragment of Human Immunoglobulin G: the Energy Landscape Analysis of a Hot Spot at the Intermolecular Interface," Proteins: Structure, Function, and Genetics, 2002, 48(1):539-557.
Åkerström et al., "Protein G: A Powerful Tool for Binding and Detection of Monoclonal and Polyclonal Antibodies," J. Immun., Oct. 1985, 135(4):2589-2592.
Ey et al., "Isolation of Pure $IgG_1$, $IgG_{2a}$ and $IgG_{2b}$ Immunoglobulins from Mouse Serum Using Protein A-Sepharose," Immunochemistry, 1978, 15(7), 429-436.
Fassina et al., "Affinity Purification of Immunoglobulins Using Protein A Mimetic (PAM)," The Protein Protocols Handbook, Second Edition, 2002, 1013-1024.
Fassina et al., "Protein A Mimetic Peptide Ligand for Affinity Purification of Antibodies," J. Mol. Recognit., 1996, 9(5-6):564-569.
Li et al., "Design, synthesis, and application of a Protein A mimetic," Nature Biotechnology, Feb. 1998, 16(2):190-195.

* cited by examiner

*Primary Examiner* — Christina Bradley
(74) *Attorney, Agent, or Firm* — Foley & Lardner LLP

(57) ABSTRACT

Provided is a peptide that specifically or selectively binds to human IgG. This peptide comprises an amino acid sequence consisting of 13 to 17 amino acid residues and is capable of binding to human IgG, wherein the amino acid sequence is represented by formula I: $(X_{1-3})$-C-$(X_2)$-H-R-G-(Xaa1)-L-V-W-C-$(X_{1-3})$, wherein, X each independently represents any amino acid residue except cysteine, C represents a cysteine residue, H represents a histidine residue, R represents an arginine residue, G represents a glycine residue, Xaa1 represents a glutamic acid residue or an asparagine residue, L represents a leucine residue, V represents a valine residue, and W represents a tryptophan residue.

15 Claims, 9 Drawing Sheets

|       | 2   | 5     | 10   | 15  |
|-------|-----|-------|------|-----|
| Lib-A | XXC | XXXXG | XLVWC | TXX |

(B)

| ID       | col1 | col2  | col3  | col4 | SEQ ID      |
|----------|------|-------|-------|------|-------------|
| 4-3      | REC  | AFWRG | RLVWC | TFT  | SEQ ID NO:77 |
| 4-4      | RRC  | AWHMG | NLVWC | TLQ  | SEQ ID NO:78 |
| 4-6, 34  | SSC  | SFWRG | RLVWC | TSL  | SEQ ID NO:79 |
| 4-12     | LGC  | SWHRG | ELVWC | TRL  | SEQ ID NO:80 |
| 4-16     | EVC  | SWWRG | RLVWC | TGL  | SEQ ID NO:81 |
| 4-26     | QRC  | AWHLG | SLVWC | TMM  | SEQ ID NO:82 |
| 4-28     | REC  | TWHLG | ELVWC | TGY  | SEQ ID NO:83 |
| 4-41     | PGC  | TFHLG | NLVWC | TFA  | SEQ ID NO:84 |
| 4-43     | GDC  | TYWRG | RLVWC | TLK  | SEQ ID NO:85 |
| Beads4   | DSC  | SWSFG | RLVWC | TQF  | SEQ ID NO:86 |
| Beads12  | DWC  | SWSRG | ALVWC | TDR  | SEQ ID NO:87 |
| Beads16  | PVC  | AYSRG | MLVWC | TRA  | SEQ ID NO:88 |
| Beads20  | SVC  | AVHLG | DLVWC | TVT  | SEQ ID NO:89 |
| Beads21  | LYC  | SRHMG | RLVWC | TAG  | SEQ ID NO:90 |
| Beads23  | RSC  | SYSRG | RLVWC | TRW  | SEQ ID NO:91 |
| Beads27  | FSC  | SSHLG | VLVWC | TPM  | SEQ ID NO:92 |
| Beads28  | GSC  | RWHRG | RLVWC | TGF  | SEQ ID NO:93 |
| Beads35  | QGC  | TWHMG | RLVWC | TTG  | SEQ ID NO:94 |
| Beads37  | GSC  | SWHMG | KLVWC | TDM  | SEQ ID NO:95 |
|          |      |       |       |      |             |
|          | S    | SWHR  | R     |      |             |
|          | V    | AFSL  | E     |      |             |
|          | E    | TYWM  | N     |      |             |
|          |      | R     |       |      |             |

Fig. 3

Lib-B

| Number | 3 | 4 | 5 | 6 | 7 | 8 | 9 | 10 | 11 | 12 | 13 | 14 | 15 | SEQ ID NO:96 |
|---|---|---|---|---|---|---|---|---|---|---|---|---|---|---|
| DNA 5'– | GAT | TGT | DCY | TDS | NRS | WKS | GGT | VAS | TDS | RYY | YDS | TGT | ACT –3' | |
| | D | C | A | W | H | L | G | N | L | V | W | C | T | |
| | | | | T | Y | M | | D | F | I | H | | | |
| | | | | S | F | S | R | E | Y | T | F | | | |
| | | | | | L | D | F | Q | W | A | Y | | | |
| | | | | | C | Q | C | H | C | L | | | | |
| | | | | | * | Y | W | K | * | Q | | | | |
| | | | | | | C | I | | | R | | | | |
| | | | | | | R | S | | | C | | | | |
| | | | | | | N | | | | * | | | | |
| | | | | | | K | | | | | | | | |
| | | | | | | G | | | | | | | | |
| | | | | | | E | | | | | | | | |
| | | | | | | * | | | | | | | | |

Symbol "*" indicates inclusion of stop codon.

Fig. 4

Lib-C

| Number | DNA | 2 | 3 | 4 | 5 | 6 | 7 | 8 | 9 | 10 | 11 | 12 | 13 | 14 | 15 | 16 | 17 | SEQ ID NO:97 |
|---|---|---|---|---|---|---|---|---|---|---|---|---|---|---|---|---|---|---|
| | 5'- | NNK | RRN | TGT | DCY | TDS | YAH | YKS | GGT | VRW | WTS | RBY | YDS | TGT | RBY | NNK | NNK -3' | |
| | | X | D | C | A | W | H | L | G | R | L | V | W | C | T | X | X | |
| | | E | T | Y | Y | F | N | F | I | H | S | | | | | | | |
| | | S | S | F | Q | R | E | I | T | F | V | | | | | | | |
| | | R | L | * | C | D | M | S | Y | I | | | | | | | | |
| | | N | C | W | H | G | L | A | | | | | | | | | | |
| | | K | * | K | A | C | G | | | | | | | | | | | |
| | | G | S | R | | | | | | | | | | | | | | |
| | | | Q | Q | | | | | | | | | | | | | | |
| | | | G | * | | | | | | | | | | | | | | |

Symbol "*" indicates inclusion of stop codon.

Fig. 6

| Number | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|
| Amino acid | X | X | X | C | A | Y | H | R | G | E | L | V | W | C | X | X | X | SEQ ID NO:98 |
| DNA | NNN | NNN | NNN | TGT | GCA | TAC | CAT | CGG | GGA | GAA | TTG | GTT | TGG | TGT | NNN | NNN | NNN | SEQ ID NO:99 |
| | XYZ | XYZ | XYZ | TGT | GCA | TAC | CAT | CGG | GGA | GAA | TTG | GTT | TGG | TGT | XYZ | XYZ | XYZ | |

X, Y, and Z each represent mixed nucleotides of the following ratios
X: G 38%, A 19%, T 26%, C 17%
Y: G 31%, A 34%, T 17%, C 18%
Z: G 24%, C 76%

Fig. 7

| GFc-C35 | G | P | D | C | T | Y | T | N | G | N | L | V | W | C | T | F | H | SEQ ID NO:4 |
|---|---|---|---|---|---|---|---|---|---|---|---|---|---|---|---|---|---|---|
| C35A-3/15 | | D | C | A | Y | H | R | G | E | L | V | W | C | T | | | | SEQ ID NO:52 |
| Frequency of appearance of amino acid | S28 | D22 | S28 | | | | | | | | | | | | S56 | H28 | Y33 | |
| | G17 | G17 | D17 | | | | | | | | | | | | T11 | G17 | F28 | |
| | F11 | S11 | T11 | | | | | | | | | | | | D11 | Y11 | H11 | |
| | H6 | A11 | N11 | | | | | | | | | | | | G6 | T11 | M11 | |
| | N6 | N6 | E11 | | | | | | | | | | | | E6 | N11 | L6 | |
| | V6 | Y6 | P6 | | | | | | | | | | | | | D11 | S6 | |
| | L6 | E6 | Y6 | | | | | | | | | | | | | F6 | D6 | |
| | D6 | V6 | Q6 | | | | | | | | | | | | | V6 | | |
| | R6 | H6 | R6 | | | | | | | | | | | | | | | |
| | E6 | F6 | | | | | | | | | | | | | | | | |
| | T6 | R6 | | | | | | | | | | | | | | | | |

SEQUENCE LISTING

```
<160> NUMBER OF SEQ ID NOS: 108

<210> SEQ ID NO 1
<211> LENGTH: 18
<212> TYPE: PRT
<213> ORGANISM: Artificial
<220> FEATURE:
<223> OTHER INFORMATION: IgG-binding peptide

<400> SEQUENCE: 1

Ser Phe Thr Cys Ala Tyr Asp Arg Asp Gly Asn Leu Val Trp Cys Thr
1               5                   10                  15

His Ser

<210> SEQ ID NO 2
<211> LENGTH: 17
<212> TYPE: PRT
<213> ORGANISM: Artificial
<220> FEATURE:
<223> OTHER INFORMATION: IgG-binding peptide

<400> SEQUENCE: 2

Ser Ser Asp Cys Thr Tyr Gln Arg Gly Glu Leu Val Trp Cys Thr His
1               5                   10                  15

Leu

<210> SEQ ID NO 3
<211> LENGTH: 17
<212> TYPE: PRT
<213> ORGANISM: Artificial
<220> FEATURE:
<223> OTHER INFORMATION: IgG-binding peptide

<400> SEQUENCE: 3

Pro Gly Glu Cys Thr Lys His Met Gly Glu Leu Val Trp Cys Val Ser
1               5                   10                  15

Lys

<210> SEQ ID NO 4
<211> LENGTH: 17
<212> TYPE: PRT
<213> ORGANISM: Artificial
<220> FEATURE:
<223> OTHER INFORMATION: IgG-binding peptide

<400> SEQUENCE: 4

Gly Pro Asp Cys Thr Tyr Thr Asn Gly Asn Leu Val Trp Cys Thr Phe
1               5                   10                  15
```

His

<210> SEQ ID NO 5
<211> LENGTH: 17
<212> TYPE: PRT
<213> ORGANISM: Artificial
<220> FEATURE:
<223> OTHER INFORMATION: IgG-binding peptide

<400> SEQUENCE: 5

Lys Pro Arg Cys Ser Tyr Leu Arg Gly Gln Leu Val Trp Cys Leu His
1               5                   10                  15

Ser

<210> SEQ ID NO 6
<211> LENGTH: 13
<212> TYPE: PRT
<213> ORGANISM: Artificial
<220> FEATURE:
<223> OTHER INFORMATION: IgG-binding peptide

<400> SEQUENCE: 6

Asp Cys Ser Tyr Arg Phe Gly Glu Leu Val Trp Cys Thr
1               5                   10

<210> SEQ ID NO 7
<211> LENGTH: 13
<212> TYPE: PRT
<213> ORGANISM: Artificial
<220> FEATURE:
<223> OTHER INFORMATION: IgG-binding peptide

<400> SEQUENCE: 7

Asp Cys Ser Tyr His Phe Gly Glu Leu Val Trp Cys Thr
1               5                   10

<210> SEQ ID NO 8
<211> LENGTH: 13
<212> TYPE: PRT
<213> ORGANISM: Artificial
<220> FEATURE:
<223> OTHER INFORMATION: IgG-binding peptide

<400> SEQUENCE: 8

Asp Cys Ala Phe His Leu Gly His Leu Val Trp Cys Thr
1               5                   10

<210> SEQ ID NO 9
<211> LENGTH: 13
<212> TYPE: PRT
<213> ORGANISM: Artificial
<220> FEATURE:
<223> OTHER INFORMATION: IgG-binding peptide

<400> SEQUENCE: 9

Asp Cys Ala Phe His Arg Gly Asp Leu Val Trp Cys Thr
1               5                   10

<210> SEQ ID NO 10
<211> LENGTH: 13
<212> TYPE: PRT
<213> ORGANISM: Artificial
<220> FEATURE:
<223> OTHER INFORMATION: IgG-binding peptide

<400> SEQUENCE: 10

```
Asp Cys Ala Phe His Phe Gly Asp Leu Val Trp Cys Thr
1               5                   10
```

<210> SEQ ID NO 11
<211> LENGTH: 13
<212> TYPE: PRT
<213> ORGANISM: Artificial
<220> FEATURE:
<223> OTHER INFORMATION: IgG-binding peptide

<400> SEQUENCE: 11

```
Asp Cys Thr Tyr His Phe Gly Lys Leu Val Trp Cys Thr
1               5                   10
```

<210> SEQ ID NO 12
<211> LENGTH: 13
<212> TYPE: PRT
<213> ORGANISM: Artificial
<220> FEATURE:
<223> OTHER INFORMATION: IgG-binding peptide

<400> SEQUENCE: 12

```
Asp Cys Ala Phe His Leu Gly Glu Leu Val Arg Cys Thr
1               5                   10
```

<210> SEQ ID NO 13
<211> LENGTH: 13
<212> TYPE: PRT
<213> ORGANISM: Artificial
<220> FEATURE:
<223> OTHER INFORMATION: IgG-binding peptide

<400> SEQUENCE: 13

```
Asp Cys Thr Trp Lys Phe Gly Asp Leu Ile Trp Cys Thr
1               5                   10
```

<210> SEQ ID NO 14
<211> LENGTH: 13
<212> TYPE: PRT
<213> ORGANISM: Artificial
<220> FEATURE:
<223> OTHER INFORMATION: IgG-binding peptide

<400> SEQUENCE: 14

```
Asp Cys Ala Tyr His Leu Gly Gln Leu Val Arg Cys Thr
1               5                   10
```

<210> SEQ ID NO 15
<211> LENGTH: 13
<212> TYPE: PRT
<213> ORGANISM: Artificial
<220> FEATURE:
<223> OTHER INFORMATION: IgG-binding peptide

<400> SEQUENCE: 15

```
Asp Cys Ser Phe His Leu Gly Asp Leu Val Trp Cys Thr
1               5                   10
```

<210> SEQ ID NO 16
<211> LENGTH: 13
<212> TYPE: PRT
<213> ORGANISM: Artificial
<220> FEATURE:
<223> OTHER INFORMATION: IgG-binding peptide

<400> SEQUENCE: 16

```
Asp Cys Ser Tyr His Leu Gly Asp Tyr Val Trp Cys Thr
1               5                   10
```

<210> SEQ ID NO 17
<211> LENGTH: 13
<212> TYPE: PRT
<213> ORGANISM: Artificial
<220> FEATURE:
<223> OTHER INFORMATION: IgG-binding peptide

<400> SEQUENCE: 17

```
Asp Cys Ser Trp His Met Gly Gln Leu Ile Trp Cys Thr
1               5                   10
```

<210> SEQ ID NO 18
<211> LENGTH: 16
<212> TYPE: PRT
<213> ORGANISM: Artificial
<220> FEATURE:
<223> OTHER INFORMATION: IgG-binding peptide

<400> SEQUENCE: 18

```
Arg Gly Cys Ser Tyr His Leu Gly Gln Leu Val Trp Cys Thr Ala Val
1               5                   10                  15
```

<210> SEQ ID NO 19
<211> LENGTH: 16
<212> TYPE: PRT
<213> ORGANISM: Artificial
<220> FEATURE:
<223> OTHER INFORMATION: IgG-binding peptide

<400> SEQUENCE: 19

```
Val Lys Cys Ser Trp His Leu Gly Gln Met Val Trp Cys Thr Ser Asn
1               5                   10                  15
```

<210> SEQ ID NO 20
<211> LENGTH: 16
<212> TYPE: PRT
<213> ORGANISM: Artificial
<220> FEATURE:
<223> OTHER INFORMATION: IgG-binding peptide

<400> SEQUENCE: 20

```
Ala Asn Cys Ser Trp His Leu Gly Asp Met Val Trp Cys Ser Thr Ile
1               5                   10                  15
```

<210> SEQ ID NO 21
<211> LENGTH: 16
<212> TYPE: PRT
<213> ORGANISM: Artificial
<220> FEATURE:
<223> OTHER INFORMATION: IgG-binding peptide

<400> SEQUENCE: 21

```
Val Lys Cys Ser Trp His Leu Gly Gln Met Val Trp Cys Ser Asn Ser
1               5                   10                  15
```

<210> SEQ ID NO 22
<211> LENGTH: 16
<212> TYPE: PRT
<213> ORGANISM: Artificial
<220> FEATURE:
<223> OTHER INFORMATION: IgG-binding peptide

<400> SEQUENCE: 22

```
Val Lys Cys Ser Trp His Leu Gly Gln Met Val Trp Cys Ser Asn Ser
```

<210> SEQ ID NO 23
<211> LENGTH: 16
<212> TYPE: PRT
<213> ORGANISM: Artificial
<220> FEATURE:
<223> OTHER INFORMATION: IgG-binding peptide

<400> SEQUENCE: 23

Leu Asn Cys Ala Phe His Arg Gly Arg Leu Val Trp Cys Thr Asp Leu
1               5                   10                  15

<210> SEQ ID NO 24
<211> LENGTH: 14
<212> TYPE: PRT
<213> ORGANISM: Artificial
<220> FEATURE:
<223> OTHER INFORMATION: IgG-binding peptide

<400> SEQUENCE: 24

Ser Lys Cys Ser Phe His Leu Gly Gln Leu Ile Trp Cys Ser
1               5                   10

<210> SEQ ID NO 25
<211> LENGTH: 16
<212> TYPE: PRT
<213> ORGANISM: Artificial
<220> FEATURE:
<223> OTHER INFORMATION: IgG-binding peptide

<400> SEQUENCE: 25

Thr Arg Cys Ser Tyr His Leu Gly Glu Met Val Trp Cys Ala Pro Ser
1               5                   10                  15

<210> SEQ ID NO 26
<211> LENGTH: 16
<212> TYPE: PRT
<213> ORGANISM: Artificial
<220> FEATURE:
<223> OTHER INFORMATION: IgG-binding peptide

<400> SEQUENCE: 26

Leu Asn Cys Ala Phe His Arg Gly Arg Leu Val Trp Cys Thr Asp Leu
1               5                   10                  15

<210> SEQ ID NO 27
<211> LENGTH: 16
<212> TYPE: PRT
<213> ORGANISM: Artificial
<220> FEATURE:
<223> OTHER INFORMATION: IgG-binding peptide

<400> SEQUENCE: 27

Val Gly Cys Ala Tyr His Leu Gly Asn Met Val Trp Cys Thr Ser Phe
1               5                   10                  15

<210> SEQ ID NO 28
<211> LENGTH: 15
<212> TYPE: PRT
<213> ORGANISM: Artificial
<220> FEATURE:
<223> OTHER INFORMATION: IgG-binding peptide

<400> SEQUENCE: 28

Pro Asp Cys Thr Tyr Thr Asn Gly Asn Leu Val Trp Cys Thr Phe
1               5                   10                  15

<210> SEQ ID NO 29
<211> LENGTH: 13
<212> TYPE: PRT
<213> ORGANISM: Artificial
<220> FEATURE:
<223> OTHER INFORMATION: IgG-binding peptide

<400> SEQUENCE: 29

Asp Cys Thr Tyr Thr Asn Gly Asn Leu Val Trp Cys Thr
1               5                   10

<210> SEQ ID NO 30
<211> LENGTH: 13
<212> TYPE: PRT
<213> ORGANISM: Artificial
<220> FEATURE:
<223> OTHER INFORMATION: IgG-binding peptide

<400> SEQUENCE: 30

Arg Cys Thr Tyr Thr Asn Gly Asn Leu Val Trp Cys Thr
1               5                   10

<210> SEQ ID NO 31
<211> LENGTH: 13
<212> TYPE: PRT
<213> ORGANISM: Artificial
<220> FEATURE:
<223> OTHER INFORMATION: IgG-binding peptide

<400> SEQUENCE: 31

Asp Cys Ala Tyr Thr Asn Gly Asn Leu Val Trp Cys Thr
1               5                   10

<210> SEQ ID NO 32
<211> LENGTH: 13
<212> TYPE: PRT
<213> ORGANISM: Artificial
<220> FEATURE:
<223> OTHER INFORMATION: IgG-binding peptide

<400> SEQUENCE: 32

Asp Cys Ser Tyr Thr Asn Gly Asn Leu Val Trp Cys Thr
1               5                   10

<210> SEQ ID NO 33
<211> LENGTH: 13
<212> TYPE: PRT
<213> ORGANISM: Artificial
<220> FEATURE:
<223> OTHER INFORMATION: IgG-binding peptide

<400> SEQUENCE: 33

Asp Cys Thr Phe Thr Asn Gly Asn Leu Val Trp Cys Thr
1               5                   10

<210> SEQ ID NO 34
<211> LENGTH: 13
<212> TYPE: PRT
<213> ORGANISM: Artificial
<220> FEATURE:
<223> OTHER INFORMATION: IgG-binding peptide

<400> SEQUENCE: 34

Asp Cys Thr Trp Thr Asn Gly Asn Leu Val Trp Cys Thr
1               5                   10

```
<210> SEQ ID NO 35
<211> LENGTH: 13
<212> TYPE: PRT
<213> ORGANISM: Artificial
<220> FEATURE:
<223> OTHER INFORMATION: IgG-binding peptide

<400> SEQUENCE: 35

Asp Cys Thr Tyr His Asn Gly Asn Leu Val Trp Cys Thr
1               5                   10

<210> SEQ ID NO 36
<211> LENGTH: 13
<212> TYPE: PRT
<213> ORGANISM: Artificial
<220> FEATURE:
<223> OTHER INFORMATION: IgG-binding peptide

<400> SEQUENCE: 36

Asp Cys Thr Tyr Arg Asn Gly Asn Leu Val Trp Cys Thr
1               5                   10

<210> SEQ ID NO 37
<211> LENGTH: 13
<212> TYPE: PRT
<213> ORGANISM: Artificial
<220> FEATURE:
<223> OTHER INFORMATION: IgG-binding peptide

<400> SEQUENCE: 37

Asp Cys Thr Tyr Ser Asn Gly Asn Leu Val Trp Cys Thr
1               5                   10

<210> SEQ ID NO 38
<211> LENGTH: 13
<212> TYPE: PRT
<213> ORGANISM: Artificial
<220> FEATURE:
<223> OTHER INFORMATION: IgG-binding peptide

<400> SEQUENCE: 38

Asp Cys Thr Tyr Thr Leu Gly Asn Leu Val Trp Cys Thr
1               5                   10

<210> SEQ ID NO 39
<211> LENGTH: 13
<212> TYPE: PRT
<213> ORGANISM: Artificial
<220> FEATURE:
<223> OTHER INFORMATION: IgG-binding peptide

<400> SEQUENCE: 39

Asp Cys Thr Tyr Thr Arg Gly Asn Leu Val Trp Cys Thr
1               5                   10

<210> SEQ ID NO 40
<211> LENGTH: 13
<212> TYPE: PRT
<213> ORGANISM: Artificial
<220> FEATURE:
<223> OTHER INFORMATION: IgG-binding peptide

<400> SEQUENCE: 40

Asp Cys Thr Tyr Thr Asn Gly Glu Leu Val Trp Cys Thr
1               5                   10
```

-continued

```
<210> SEQ ID NO 41
<211> LENGTH: 13
<212> TYPE: PRT
<213> ORGANISM: Artificial
<220> FEATURE:
<223> OTHER INFORMATION: IgG-binding peptide

<400> SEQUENCE: 41

Asp Cys Thr Tyr Thr Asn Gly Arg Leu Val Trp Cys Thr
1               5                   10

<210> SEQ ID NO 42
<211> LENGTH: 13
<212> TYPE: PRT
<213> ORGANISM: Artificial
<220> FEATURE:
<223> OTHER INFORMATION: IgG-binding peptide

<400> SEQUENCE: 42

Asp Cys Thr Tyr Thr Asn Gly Asp Leu Val Trp Cys Thr
1               5                   10

<210> SEQ ID NO 43
<211> LENGTH: 13
<212> TYPE: PRT
<213> ORGANISM: Artificial
<220> FEATURE:
<223> OTHER INFORMATION: IgG-binding peptide

<400> SEQUENCE: 43

Asp Cys Thr Tyr Thr Asn Gly Gln Leu Val Trp Cys Thr
1               5                   10

<210> SEQ ID NO 44
<211> LENGTH: 13
<212> TYPE: PRT
<213> ORGANISM: Artificial
<220> FEATURE:
<223> OTHER INFORMATION: IgG-binding peptide

<400> SEQUENCE: 44

Asp Cys Thr Tyr Thr Asn Gly Asn Met Val Trp Cys Thr
1               5                   10

<210> SEQ ID NO 45
<211> LENGTH: 13
<212> TYPE: PRT
<213> ORGANISM: Artificial
<220> FEATURE:
<223> OTHER INFORMATION: IgG-binding peptide

<400> SEQUENCE: 45

Asp Cys Thr Tyr Thr Asn Gly Asn Leu Ile Trp Cys Thr
1               5                   10

<210> SEQ ID NO 46
<211> LENGTH: 13
<212> TYPE: PRT
<213> ORGANISM: Artificial
<220> FEATURE:
<223> OTHER INFORMATION: IgG-binding peptide

<400> SEQUENCE: 46

Asp Cys Thr Tyr Thr Asn Gly Asn Leu Val Trp Cys Ser
1               5                   10

<210> SEQ ID NO 47
```

```
<211> LENGTH: 13
<212> TYPE: PRT
<213> ORGANISM: Artificial
<220> FEATURE:
<223> OTHER INFORMATION: IgG-binding peptide

<400> SEQUENCE: 47

Asp Cys Thr Tyr His Arg Gly Asn Leu Val Trp Cys Thr
1               5                   10

<210> SEQ ID NO 48
<211> LENGTH: 13
<212> TYPE: PRT
<213> ORGANISM: Artificial
<220> FEATURE:
<223> OTHER INFORMATION: IgG-binding peptide

<400> SEQUENCE: 48

Asp Cys Ala Tyr His Arg Gly Asn Leu Val Trp Cys Thr
1               5                   10

<210> SEQ ID NO 49
<211> LENGTH: 13
<212> TYPE: PRT
<213> ORGANISM: Artificial
<220> FEATURE:
<223> OTHER INFORMATION: IgG-binding peptide

<400> SEQUENCE: 49

Asp Cys Thr Trp His Arg Gly Asn Leu Val Trp Cys Thr
1               5                   10

<210> SEQ ID NO 50
<211> LENGTH: 13
<212> TYPE: PRT
<213> ORGANISM: Artificial
<220> FEATURE:
<223> OTHER INFORMATION: IgG-binding peptide

<400> SEQUENCE: 50

Asp Cys Thr Tyr His Arg Gly Glu Leu Val Trp Cys Thr
1               5                   10

<210> SEQ ID NO 51
<211> LENGTH: 13
<212> TYPE: PRT
<213> ORGANISM: Artificial
<220> FEATURE:
<223> OTHER INFORMATION: IgG-binding peptide

<400> SEQUENCE: 51

Asp Cys Thr Tyr His Arg Gly Asn Leu Ile Trp Cys Thr
1               5                   10

<210> SEQ ID NO 52
<211> LENGTH: 13
<212> TYPE: PRT
<213> ORGANISM: Artificial
<220> FEATURE:
<223> OTHER INFORMATION: IgG-binding peptide

<400> SEQUENCE: 52

Asp Cys Ala Tyr His Arg Gly Glu Leu Val Trp Cys Thr
1               5                   10

<210> SEQ ID NO 53
<211> LENGTH: 13
```

```
<212> TYPE: PRT
<213> ORGANISM: Artificial
<220> FEATURE:
<223> OTHER INFORMATION: IgG-binding peptide

<400> SEQUENCE: 53

Asp Cys Ala Trp His Arg Gly Glu Leu Val Trp Cys Thr
1               5                   10

<210> SEQ ID NO 54
<211> LENGTH: 13
<212> TYPE: PRT
<213> ORGANISM: Artificial
<220> FEATURE:
<223> OTHER INFORMATION: IgG-binding peptide

<400> SEQUENCE: 54

Arg Cys Ala Tyr His Arg Gly Glu Leu Val Trp Cys Ser
1               5                   10

<210> SEQ ID NO 55
<211> LENGTH: 13
<212> TYPE: PRT
<213> ORGANISM: Artificial
<220> FEATURE:
<223> OTHER INFORMATION: IgG-binding peptide

<400> SEQUENCE: 55

Asp Cys Ala Tyr His Arg Gly Glu Leu Val Trp Cys Thr
1               5                   10

<210> SEQ ID NO 56
<211> LENGTH: 17
<212> TYPE: PRT
<213> ORGANISM: Artificial
<220> FEATURE:
<223> OTHER INFORMATION: IgG-binding peptide

<400> SEQUENCE: 56

Gly Pro Asp Cys Ala Tyr His Arg Gly Glu Leu Val Trp Cys Thr Phe
1               5                   10                  15

His

<210> SEQ ID NO 57
<211> LENGTH: 13
<212> TYPE: PRT
<213> ORGANISM: Artificial
<220> FEATURE:
<223> OTHER INFORMATION: IgG-binding peptide

<400> SEQUENCE: 57

Arg Cys Ala Tyr His Arg Gly Glu Leu Val Trp Cys Ser
1               5                   10

<210> SEQ ID NO 58
<211> LENGTH: 17
<212> TYPE: PRT
<213> ORGANISM: Artificial
<220> FEATURE:
<223> OTHER INFORMATION: IgG-binding peptide

<400> SEQUENCE: 58

Gly Pro Arg Cys Ala Tyr His Arg Gly Glu Leu Val Trp Cys Ser Phe
1               5                   10                  15

His
```

```
<210> SEQ ID NO 59
<211> LENGTH: 17
<212> TYPE: PRT
<213> ORGANISM: Artificial
<220> FEATURE:
<223> OTHER INFORMATION: IgG-binding peptide

<400> SEQUENCE: 59

Asn Asp Thr Cys Ala Tyr His Arg Gly Glu Leu Val Trp Cys Thr Tyr
1               5                   10                  15

Ser

<210> SEQ ID NO 60
<211> LENGTH: 17
<212> TYPE: PRT
<213> ORGANISM: Artificial
<220> FEATURE:
<223> OTHER INFORMATION: IgG-binding peptide

<400> SEQUENCE: 60

Ser Asp Ser Cys Ala Tyr His Arg Gly Glu Leu Val Trp Cys Asp Gly
1               5                   10                  15

Tyr

<210> SEQ ID NO 61
<211> LENGTH: 17
<212> TYPE: PRT
<213> ORGANISM: Artificial
<220> FEATURE:
<223> OTHER INFORMATION: IgG-binding peptide

<400> SEQUENCE: 61

Val Asp Ser Cys Ala Tyr His Arg Gly Glu Leu Val Trp Cys Ser Asn
1               5                   10                  15

Tyr

<210> SEQ ID NO 62
<211> LENGTH: 17
<212> TYPE: PRT
<213> ORGANISM: Artificial
<220> FEATURE:
<223> OTHER INFORMATION: IgG-binding peptide

<400> SEQUENCE: 62

Ser Ala Glu Cys Ala Tyr His Arg Gly Glu Leu Val Trp Cys Ser Val
1               5                   10                  15

Phe

<210> SEQ ID NO 63
<211> LENGTH: 17
<212> TYPE: PRT
<213> ORGANISM: Artificial
<220> FEATURE:
<223> OTHER INFORMATION: IgG-binding peptide

<400> SEQUENCE: 63

Phe Asn Asp Cys Ala Tyr His Arg Gly Glu Leu Val Trp Cys Ser Gly
1               5                   10                  15

Tyr

<210> SEQ ID NO 64
<211> LENGTH: 17
<212> TYPE: PRT
```

```
<213> ORGANISM: Artificial
<220> FEATURE:
<223> OTHER INFORMATION: IgG-binding peptide

<400> SEQUENCE: 64

His Glu Thr Cys Ala Tyr His Arg Gly Glu Leu Val Trp Cys Asp His
1               5                   10                  15

His

<210> SEQ ID NO 65
<211> LENGTH: 17
<212> TYPE: PRT
<213> ORGANISM: Artificial
<220> FEATURE:
<223> OTHER INFORMATION: IgG-binding peptide

<400> SEQUENCE: 65

Ser Tyr Glu Cys Ala Tyr His Arg Gly Glu Leu Val Trp Cys Ser Thr
1               5                   10                  15

Tyr

<210> SEQ ID NO 66
<211> LENGTH: 17
<212> TYPE: PRT
<213> ORGANISM: Artificial
<220> FEATURE:
<223> OTHER INFORMATION: IgG-binding peptide

<400> SEQUENCE: 66

Ser Gly Asn Cys Ala Tyr His Arg Gly Glu Leu Val Trp Cys Asn Phe
1               5                   10                  15

Leu

<210> SEQ ID NO 67
<211> LENGTH: 17
<212> TYPE: PRT
<213> ORGANISM: Artificial
<220> FEATURE:
<223> OTHER INFORMATION: IgG-binding peptide

<400> SEQUENCE: 67

Ser Gly Asp Cys Ala Tyr His Arg Gly Glu Leu Val Trp Cys Ser Tyr
1               5                   10                  15

His

<210> SEQ ID NO 68
<211> LENGTH: 17
<212> TYPE: PRT
<213> ORGANISM: Artificial
<220> FEATURE:
<223> OTHER INFORMATION: IgG-binding peptide

<400> SEQUENCE: 68

Leu Ser Ser Cys Ala Tyr His Arg Gly Glu Leu Val Trp Cys Ser His
1               5                   10                  15

Phe

<210> SEQ ID NO 69
<211> LENGTH: 17
<212> TYPE: PRT
<213> ORGANISM: Artificial
<220> FEATURE:
<223> OTHER INFORMATION: IgG-binding peptide
```

```
<400> SEQUENCE: 69

Phe Ser Asp Cys Ala Tyr His Arg Gly Glu Leu Val Trp Cys Gly His
1               5                   10                  15

Phe

<210> SEQ ID NO 70
<211> LENGTH: 17
<212> TYPE: PRT
<213> ORGANISM: Artificial
<220> FEATURE:
<223> OTHER INFORMATION: IgG-binding peptide

<400> SEQUENCE: 70

Gly Asp Pro Cys Ala Tyr His Arg Gly Glu Leu Val Trp Cys Ser Asn
1               5                   10                  15

Phe

<210> SEQ ID NO 71
<211> LENGTH: 17
<212> TYPE: PRT
<213> ORGANISM: Artificial
<220> FEATURE:
<223> OTHER INFORMATION: IgG-binding peptide

<400> SEQUENCE: 71

Asp Val Tyr Cys Ala Tyr His Arg Gly Glu Leu Val Trp Cys Asn Gly
1               5                   10                  15

Asp

<210> SEQ ID NO 72
<211> LENGTH: 17
<212> TYPE: PRT
<213> ORGANISM: Artificial
<220> FEATURE:
<223> OTHER INFORMATION: IgG-binding peptide

<400> SEQUENCE: 72

Gly His Ser Cys Ala Tyr His Arg Gly Glu Leu Val Trp Cys Ser His
1               5                   10                  15

Met

<210> SEQ ID NO 73
<211> LENGTH: 17
<212> TYPE: PRT
<213> ORGANISM: Artificial
<220> FEATURE:
<223> OTHER INFORMATION: IgG-binding peptide

<400> SEQUENCE: 73

Arg Gly Gln Cys Ala Tyr His Arg Gly Glu Leu Val Trp Cys Ser His
1               5                   10                  15

Tyr

<210> SEQ ID NO 74
<211> LENGTH: 17
<212> TYPE: PRT
<213> ORGANISM: Artificial
<220> FEATURE:
<223> OTHER INFORMATION: IgG-binding peptide

<400> SEQUENCE: 74

Glu Phe Asn Cys Ala Tyr His Arg Gly Glu Leu Val Trp Cys Thr Asp
1               5                   10                  15
```

Tyr

<210> SEQ ID NO 75
<211> LENGTH: 17
<212> TYPE: PRT
<213> ORGANISM: Artificial
<220> FEATURE:
<223> OTHER INFORMATION: IgG-binding peptide

<400> SEQUENCE: 75

Gly Arg Ser Cys Ala Tyr His Arg Gly Glu Leu Val Trp Cys Ser Thr
1               5                   10                  15

Phe

<210> SEQ ID NO 76
<211> LENGTH: 17
<212> TYPE: PRT
<213> ORGANISM: Artificial
<220> FEATURE:
<223> OTHER INFORMATION: IgG-binding peptide

<400> SEQUENCE: 76

Thr Ala Arg Cys Ala Tyr His Arg Gly Glu Leu Val Trp Cys Glu Asp
1               5                   10                  15

Met

<210> SEQ ID NO 77
<211> LENGTH: 16
<212> TYPE: PRT
<213> ORGANISM: Artificial
<220> FEATURE:
<223> OTHER INFORMATION: IgG-binding peptide

<400> SEQUENCE: 77

Arg Glu Cys Ala Phe Trp Arg Gly Arg Leu Val Trp Cys Thr Phe Thr
1               5                   10                  15

<210> SEQ ID NO 78
<211> LENGTH: 16
<212> TYPE: PRT
<213> ORGANISM: Artificial
<220> FEATURE:
<223> OTHER INFORMATION: IgG-binding peptide

<400> SEQUENCE: 78

Arg Arg Cys Ala Trp His Met Gly Asn Leu Val Trp Cys Thr Leu Gln
1               5                   10                  15

<210> SEQ ID NO 79
<211> LENGTH: 16
<212> TYPE: PRT
<213> ORGANISM: Artificial
<220> FEATURE:
<223> OTHER INFORMATION: IgG-binding peptide

<400> SEQUENCE: 79

Ser Ser Cys Ser Phe Trp Arg Gly Arg Leu Val Trp Cys Thr Ser Leu
1               5                   10                  15

<210> SEQ ID NO 80
<211> LENGTH: 16
<212> TYPE: PRT
<213> ORGANISM: Artificial
<220> FEATURE:
<223> OTHER INFORMATION: IgG-binding peptide -continued

```
<400> SEQUENCE: 80

Leu Gly Cys Ser Trp His Arg Gly Glu Leu Val Trp Cys Thr Arg Leu
1               5                   10                  15

<210> SEQ ID NO 81
<211> LENGTH: 16
<212> TYPE: PRT
<213> ORGANISM: Artificial
<220> FEATURE:
<223> OTHER INFORMATION: IgG-binding peptide

<400> SEQUENCE: 81

Glu Val Cys Ser Trp Trp Arg Gly Arg Leu Val Trp Cys Thr Gly Leu
1               5                   10                  15

<210> SEQ ID NO 82
<211> LENGTH: 16
<212> TYPE: PRT
<213> ORGANISM: Artificial
<220> FEATURE:
<223> OTHER INFORMATION: IgG-binding peptide

<400> SEQUENCE: 82

Gln Arg Cys Ala Trp His Leu Gly Ser Leu Val Trp Cys Thr Met Met
1               5                   10                  15

<210> SEQ ID NO 83
<211> LENGTH: 16
<212> TYPE: PRT
<213> ORGANISM: Artificial
<220> FEATURE:
<223> OTHER INFORMATION: IgG-binding peptide

<400> SEQUENCE: 83

Arg Glu Cys Thr Trp His Leu Gly Glu Leu Val Trp Cys Thr Gly Tyr
1               5                   10                  15

<210> SEQ ID NO 84
<211> LENGTH: 16
<212> TYPE: PRT
<213> ORGANISM: Artificial
<220> FEATURE:
<223> OTHER INFORMATION: IgG-binding peptide

<400> SEQUENCE: 84

Pro Gly Cys Thr Phe His Leu Gly Asn Leu Val Trp Cys Thr Phe Ala
1               5                   10                  15

<210> SEQ ID NO 85
<211> LENGTH: 16
<212> TYPE: PRT
<213> ORGANISM: Artificial
<220> FEATURE:
<223> OTHER INFORMATION: IgG-binding peptide

<400> SEQUENCE: 85

Gly Asp Cys Thr Tyr Trp Arg Gly Arg Leu Val Trp Cys Thr Leu Lys
1               5                   10                  15

<210> SEQ ID NO 86
<211> LENGTH: 16
<212> TYPE: PRT
<213> ORGANISM: Artificial
<220> FEATURE:
<223> OTHER INFORMATION: IgG-binding peptide
```

```
<400> SEQUENCE: 86

Asp Ser Cys Ser Trp Ser Phe Gly Arg Leu Val Trp Cys Thr Gln Phe
1               5                   10                  15

<210> SEQ ID NO 87
<211> LENGTH: 16
<212> TYPE: PRT
<213> ORGANISM: Artificial
<220> FEATURE:
<223> OTHER INFORMATION: IgG-binding peptide

<400> SEQUENCE: 87

Asp Trp Cys Ser Trp Ser Arg Gly Ala Leu Val Trp Cys Thr Asp Arg
1               5                   10                  15

<210> SEQ ID NO 88
<211> LENGTH: 16
<212> TYPE: PRT
<213> ORGANISM: Artificial
<220> FEATURE:
<223> OTHER INFORMATION: IgG-binding peptide

<400> SEQUENCE: 88

Pro Val Cys Ala Tyr Ser Arg Gly Met Leu Val Trp Cys Thr Arg Ala
1               5                   10                  15

<210> SEQ ID NO 89
<211> LENGTH: 16
<212> TYPE: PRT
<213> ORGANISM: Artificial
<220> FEATURE:
<223> OTHER INFORMATION: IgG-binding peptide

<400> SEQUENCE: 89

Ser Val Cys Ala Val His Leu Gly Asp Leu Val Trp Cys Thr Val Thr
1               5                   10                  15

<210> SEQ ID NO 90
<211> LENGTH: 16
<212> TYPE: PRT
<213> ORGANISM: Artificial
<220> FEATURE:
<223> OTHER INFORMATION: IgG-binding peptide

<400> SEQUENCE: 90

Leu Tyr Cys Ser Arg His Met Gly Arg Leu Val Trp Cys Thr Ala Gly
1               5                   10                  15

<210> SEQ ID NO 91
<211> LENGTH: 16
<212> TYPE: PRT
<213> ORGANISM: Artificial
<220> FEATURE:
<223> OTHER INFORMATION: IgG-binding peptide

<400> SEQUENCE: 91

Arg Ser Cys Ser Tyr Ser Arg Gly Arg Leu Val Trp Cys Thr Arg Trp
1               5                   10                  15

<210> SEQ ID NO 92
<211> LENGTH: 16
<212> TYPE: PRT
<213> ORGANISM: Artificial
<220> FEATURE:
<223> OTHER INFORMATION: IgG-binding peptide

<400> SEQUENCE: 92
```

```
Phe Ser Cys Ser Ser His Leu Gly Val Leu Val Trp Cys Thr Pro Met
1               5                   10                  15
```

<210> SEQ ID NO 93
<211> LENGTH: 16
<212> TYPE: PRT
<213> ORGANISM: Artificial
<220> FEATURE:
<223> OTHER INFORMATION: IgG-binding peptide

<400> SEQUENCE: 93

```
Gly Ser Cys Arg Trp His Arg Gly Arg Leu Val Trp Cys Thr Gly Phe
1               5                   10                  15
```

<210> SEQ ID NO 94
<211> LENGTH: 16
<212> TYPE: PRT
<213> ORGANISM: Artificial
<220> FEATURE:
<223> OTHER INFORMATION: IgG-binding peptide

<400> SEQUENCE: 94

```
Gln Gly Cys Thr Trp His Met Gly Arg Leu Val Trp Cys Thr Thr Gly
1               5                   10                  15
```

<210> SEQ ID NO 95
<211> LENGTH: 16
<212> TYPE: PRT
<213> ORGANISM: Artificial
<220> FEATURE:
<223> OTHER INFORMATION: IgG-binding peptide

<400> SEQUENCE: 95

```
Gly Ser Cys Ser Trp His Met Gly Lys Leu Val Trp Cys Thr Asp Met
1               5                   10                  15
```

<210> SEQ ID NO 96
<211> LENGTH: 39
<212> TYPE: DNA
<213> ORGANISM: Artificial
<220> FEATURE:
<223> OTHER INFORMATION: recombinant DNA
<220> FEATURE:
<221> NAME/KEY: misc_feature
<222> LOCATION: (13)..(13)
<223> OTHER INFORMATION: n is a, c, g, or t

<400> SEQUENCE: 96
gattgtdcyt dsnrswksgg tvastdsryy ydstgtact                   39

<210> SEQ ID NO 97
<211> LENGTH: 48
<212> TYPE: DNA
<213> ORGANISM: Artificial
<220> FEATURE:
<223> OTHER INFORMATION: recombinant DNA
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:

```
<221> NAME/KEY: misc_feature
<222> LOCATION: (46)..(47)
<223> OTHER INFORMATION: n is a, c, g, or t

<400> SEQUENCE: 97
nnkrrntgtd cytdsyahyk sggtvrwwts rbyydstgtr bynnknnk                48

<210> SEQ ID NO 98
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 98

Xaa Xaa Xaa Cys Ala Tyr His Arg Gly Glu Leu Val Trp Cys Xaa Xaa
1               5                   10                  15

Xaa

<210> SEQ ID NO 99
<211> LENGTH: 51
<212> TYPE: DNA
<213> ORGANISM: Artificial
<220> FEATURE:
<223> OTHER INFORMATION: recombinant DNA
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)
<223> OTHER INFORMATION: n is c or g
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)
<223> OTHER INFORMATION: n is c or g
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)
<223> OTHER INFORMATION: n is c or g
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)
<223> OTHER INFORMATION: n is c or g
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)
<223> OTHER INFORMATION: n is c or g
<220> FEATURE:
```

```
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)
<223> OTHER INFORMATION: n is c or g

<400> SEQUENCE: 99
nnnnnnnnnt gtgcatacca tcggggagaa ttggtttggt gtnnnnnnnn n         51

<210> SEQ ID NO 100
<211> LENGTH: 17
<212> TYPE: PRT
<213> ORGANISM: Artificial
<220> FEATURE:
<223> OTHER INFORMATION: IgG-binding peptide

<400> SEQUENCE: 100

Ser Pro Asp Cys Ala Tyr His Arg Gly Glu Leu Val Trp Cys Thr Phe
1               5                   10                  15
His

<210> SEQ ID NO 101
<211> LENGTH: 17
<212> TYPE: PRT
<213> ORGANISM: Artificial
<220> FEATURE:
<223> OTHER INFORMATION: IgG-binding peptide

<400> SEQUENCE: 101

Gly Asp Asp Cys Ala Tyr His Arg Gly Glu Leu Val Trp Cys Thr Phe
1               5                   10                  15
His

<210> SEQ ID NO 102
<211> LENGTH: 17
<212> TYPE: PRT
<213> ORGANISM: Artificial
<220> FEATURE:
<223> OTHER INFORMATION: IgG-binding peptide

<400> SEQUENCE: 102

Gly Pro Ser Cys Ala Tyr His Arg Gly Glu Leu Val Trp Cys Thr Phe
1               5                   10                  15
His

<210> SEQ ID NO 103
<211> LENGTH: 17
<212> TYPE: PRT
<213> ORGANISM: Artificial
<220> FEATURE:
<223> OTHER INFORMATION: IgG-binding peptide

<400> SEQUENCE: 103

Gly Pro Asp Cys Ala Tyr His Arg Gly Glu Leu Val Trp Cys Ser Phe
1               5                   10                  15
His

<210> SEQ ID NO 104
<211> LENGTH: 17
<212> TYPE: PRT
<213> ORGANISM: Artificial
<220> FEATURE:
<223> OTHER INFORMATION: IgG-binding peptide
```

<400> SEQUENCE: 104

Gly Pro Asp Cys Ala Tyr His Arg Gly Glu Leu Val Trp Cys Thr His
1               5                   10                  15

His

<210> SEQ ID NO 105
<211> LENGTH: 17
<212> TYPE: PRT
<213> ORGANISM: Artificial
<220> FEATURE:
<223> OTHER INFORMATION: IgG-binding peptide

<400> SEQUENCE: 105

Gly Pro Asp Cys Ala Tyr His Arg Gly Glu Leu Val Trp Cys Thr Phe
1               5                   10                  15

Tyr

<210> SEQ ID NO 106
<211> LENGTH: 17
<212> TYPE: PRT
<213> ORGANISM: Artificial
<220> FEATURE:
<223> OTHER INFORMATION: IgG-binding peptide

<400> SEQUENCE: 106

Ser Pro Asp Cys Ala Tyr His Arg Gly Glu Leu Val Trp Cys Thr Phe
1               5                   10                  15

Tyr

<210> SEQ ID NO 107
<211> LENGTH: 17
<212> TYPE: PRT
<213> ORGANISM: Artificial
<220> FEATURE:
<223> OTHER INFORMATION: IgG-binding peptide

<400> SEQUENCE: 107

Ser Asp Asp Cys Ala Tyr His Arg Gly Glu Leu Val Trp Cys Thr Phe
1               5                   10                  15

Tyr

<210> SEQ ID NO 108
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (1)..(3)
<223> OTHER INFORMATION: Xaa each independently represents any amino
      acid residue except cysteine
<220> FEATURE:
<221> NAME/KEY: misc_feature
<222> LOCATION: (15)..(17)
<223> OTHER INFORMATION: Xaa each independently represents any amino
      acid residue except cysteine

<400> SEQUENCE: 108

Xaa Xaa Xaa Cys Ala Tyr His Arg Gly Glu Leu Val Trp Cys Xaa Xaa
1               5                   10                  15

Xaa

IGG-BINDING PEPTIDE AND METHOD FOR DETECTING AND PURIFYING IGG USING SAME

CROSS-REFERENCE TO RELATED APPLICATIONS

This application is a National Stage application of PCT/JP2012/071303, Aug. 23, 2012, which claims priority from Japanese application JP 2011-182539, filed Aug. 24, 2011.

The instant application contains a Sequence Listing which has been submitted in ASCII format via EFS-WEB and is hereby incorporated by reference is its entirety. Said ASCII copy, created on Jul. 10, 2015, is named sequence.txt and is 27 KB.

TECHNICAL FIELD

The present invention relates to a human IgG-binding peptide obtained from a random peptide library and methods for detecting and purifying IgG using the peptide.

BACKGROUND ART

Currently, antibody drugs are attracting attention as the most reliable molecular targeted drugs, making a contribution to the rapid expansion of a new pharmaceutical field. The majority of the antibody drugs currently under development or in use employ antibodies belonging to the immunoglobulin G (hereinbelow, denoted as "IgG") class.

Conventionally, protein such as *Staphylococcus aureus*-derived protein A or protein G is used for the purification of IgG antibodies (Non Patent Literatures 1 and 2). Since these proteins also bind mouse IgG as well as rabbit IgG, they have been popularly used for the purification of IgG at a laboratory reagent level. However, in light of the recent trend of the use of antibody drugs, particularly human IgG1, in the pharmaceutical field, the importance of industrial and pharmaceutical application of these proteins has been increasing more than ever. Particularly, protein A columns play a central role also in the purification of antibody drugs, and many antibody drug manufacturers have adopted a protein A column-centered purification system.

However, some problems associated with protein A columns are pointed out. One problem is the contamination of purified antibodies with protein A. Because protein A is a protein derived from bacteria, it becomes highly immunogenic when administered to the human body. Also, endotoxin contamination is a concern. Thus, in order to prevent contamination with unfavorable substances, protein A is required to be highly purified as an affinity ligand used for the purification of pharmaceutical products. This causes an increase in the cost of protein A column used for the purification of pharmaceutical products.

In order to solve this problem, the development of a new purification system for IgG antibodies is ongoing. For example, protein A mimetic peptides (Non Patent Literatures 3 and 4) and a non-peptide affinity ligand (Non Patent Literature 5) that was designed based on a X-ray crystallographic structure formed between protein A and the Fc portion of an IgG antibody have been reported. However, their use was limited due to problems associated with their binding ability and specificity.

Also, a number of studies have been undertaken in search for a novel IgG-binding peptide using, for example, phage libraries and synthetic peptide libraries (Patent Literatures 1 to 3).

As described above, research of purification of IgG antibodies using a new peptide or small molecule has been ongoing; nevertheless, no new purification system applicable on an industrial scale that can substitute a protein A or G column has yet been available, and there is still a need for a new technique for the purification of IgG antibodies in this field.

CITATION LIST

Patent Literature

Patent Literature 1: WO 01/045746
Patent Literature 2: WO 02/086070
Patent Literature 3: WO 02/38592

Non Patent Literature

Non Patent Literature 1: Ey, P. L., Prowse, S. J., and Jenkin, C. R. (1978) Immunochemistry 15 (7), 429 to 436
Non Patent Literature 2: Akerstrom, B., Brodin, T., Reis, K., and Bjorck, L. (1985) J Immunol 135 (4), 2589 to 2592
Non Patent Literature 3: Fassina, G., Verdoliva, A., Odierna, M. R., Ruvo, M., and Cassini, G. (1996) J Mol Recognit 9 (5 to 6), 564 to 569
Non Patent Literature 4: Fassina, G., Palombo, G., Verdoliva, A., and Ruvo, M. (2002) Affinity Purification of Immunoglobulins Using Protein A Mimetic (PAM) In: Walker, J. M. (ed). The Protein Protocols Handbook, Second Edition, Humana Press Inc., Totowa, N. J.
Non Patent Literature 5: Li, R., Dowd, V., Stewart, D. J., Burton, S. J., and Lowe, C. R. (1998) Nature biotechnology 16 (2), 190 to 195

SUMMARY OF INVENTION

Technical Problem

An object of the present invention is to provide a peptide that specifically or selectively binds to human IgG.

Another object of the present invention is to provide a method for purifying or analyzing (detecting or quantifying) human IgG using the peptide.

Solution to Problem

Human IgG is mainly present in the blood and plays an important role in biological defense and maintenance of homeostasis through elimination of foreign matters and antibody-dependent cellular cytotoxicity. Particularly, by virtue of these characteristics, IgG has recently been used as therapeutic antibody drugs primarily for cancer and autoimmune diseases such as rheumatism. In consideration of the situation of IgG antibody that it has started to occupy an important position as a medicine as described above, the present invention is presumed to be useful for establishing purification and analytical methods for IgG applicable as a medicine that overcome existing drawbacks such as those mentioned in Background Art by providing a peptide capable of specifically or selectively binding to human IgG (particularly, IgG1).

In summary, the present invention has the following features.

[1] A peptide comprising an amino acid sequence consisting of 13 to 17 amino acid residues, the peptide being capable of binding to human IgG, wherein the amino acid sequence is represented by the following formula I:

$$(X_{1-3})\text{-C-}(X_2)\text{-H-R-G-}(Xaa1)\text{-L-V-W-C-}(X_{1-3}) \qquad (I)$$

wherein X each independently represents any amino acid residue except cysteine,
C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue, and
W represents a tryptophan residue.

[2] The peptide according to [1], comprising an amino acid sequence consisting of 13 to 17 amino acid residues, the peptide being capable of binding to human IgG, wherein the amino acid sequence is represented by the following formula II:

$$(X_{1-3})\text{-C-}(Xaa2)\text{-}(Xaa3)\text{-H-R-G-}(Xaa1)\text{-L-V-W-C-}(X_{1-3}) \quad (II)$$

wherein X each independently represents any amino acid residue except cysteine,
C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue,
W represents a tryptophan residue,
Xaa2 represents an alanine residue, a serine residue, or a threonine residue, and
Xaa3 represents a tyrosine residue or a tryptophan residue.

[3] The peptide according to [1] or [2], comprising an amino acid sequence consisting of 13 to 17 amino acid residues, the peptide being capable of binding to human IgG, wherein the amino acid sequence is represented by the following formula III:

$$(X_{1-3})\text{-C-A-Y-H-R-G-E-L-V-W-C-}(X_{1-3}) \quad (III)$$

wherein X each independently represents any amino acid residue except cysteine,
C represents a cysteine residue,
A represents an alanine residue,
Y represents a tyrosine residue,
H represents a histidine residue,
R represents an arginine residue,
G represents a glycine residue,
E represents a glutamic acid residue,
L represents a leucine residue,
V represents a valine residue, and
W represents a tryptophan residue.

[4] The peptide according to any of [1] to [3], wherein, when the peptide is 17 amino acid residues, amino acid residues at positions 1 to 3 and 15 to 17 from an N terminus are each as follows:
amino acid residue at position 1=S, G, F, or non-existent,
amino acid residue at position 2=D, G, A, S, P, or non-existent,
amino acid residue at position 3=S, D, T, N, E, or R,
amino acid residue at position 15=S, T, or D,
amino acid residue at position 16=H, G, Y, T, N, D, F, or non-existent, and
amino acid residue at position 17=Y, F, H, M, or non-existent.

[5] The peptide according to [4], consisting of an amino acid sequence of any of the following 1) to 12):

1) DCAYHRGELVWCT (SEQ ID NO: 55)

2) GPDCAYHRGELVWCTFH (SEQ ID NO: 56)

3) RCAYHRGELVWCS (SEQ ID NO: 57)

4) GPRCAYHRGELVWCSFH (SEQ ID NO: 58)

5) SPDCAYHRGELVWCTFH (SEQ ID NO: 100)

6) GDDCAYHRGELVWCTFH (SEQ ID NO: 101)

7) GPSCAYHRGELVWCTFH (SEQ ID NO: 102)

8) GPDCAYHRGELVWCSFH (SEQ ID NO: 103)

9) GPDCAYHRGELVWCTHH (SEQ ID NO: 104)

10) GPDCAYHRGELVWCTFY (SEQ ID NO: 105)

11) SPDCAYHRGELVWCTFY, and (SEQ ID NO: 106)

12) SDDCAYHRGELVWCTFY. (SEQ ID NO: 107)

[6] The peptide according to [1] or [2], comprising an amino acid sequence consisting of 13 amino acid residues, the peptide being capable of binding to human IgG, wherein the amino acid sequence is represented by the following formula IV:

$$D\text{-C-}(Xaa2)\text{-}(Xaa3)\text{-H-R-G-}(Xaa1)\text{-L-V-W-C-T} \quad (IV)$$

wherein
D represents an aspartic acid residue,
C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue,
W represents a tryptophan residue,
T represents a threonine residue,
Xaa2 represents an alanine residue or a threonine residue, and
Xaa3 represents a tyrosine residue or a tryptophan residue.

[7] The peptide according to [6], consisting of an amino acid sequence of any of the following 1) to 4):

1) DCTYHRGNLVWCT (SEQ ID NO: 47)

2) DCAYHRGNLVWCT (SEQ ID NO: 48)

3) DCTYHRGELVWCT, and (SEQ ID NO: 50)

4) DCAWHRGELVWCT. (SEQ ID NO: 53)

[8] A peptide comprising an amino acid sequence consisting of 13 amino acid residues, the peptide being capable of binding to human IgG, wherein the amino acid sequence is represented by the following formula V:

D-C-(Xaa1)-(Xaa2)-(Xaa3)-(Xaa4)-G-(Xaa5)-L-(Xaa6)-W-C-T  (V)

wherein
D represents an aspartic acid residue,
C represents a cysteine residue,
G represents a glycine residue,
L represents a leucine residue,
W represents a tryptophan residue,
T represents a threonine residue,
Xaa1 represents an alanine residue, a serine residue, or a threonine residue,
Xaa2 represents a tryptophan residue or a tyrosine residue,
Xaa3 represents a histidine residue, an arginine residue, a serine residue, or a threonine residue,
Xaa4 represents an asparagine residue or an arginine residue,
Xaa5 represents a glutamic acid residue, an asparagine residue, an arginine residue, or an aspartic acid residue, and
Xaa6 represents an isoleucine residue or a valine residue.
[9] The peptide according to [8], consisting of an amino acid sequence of any of the following 1) to 12):

```
1) DCTYTNGNLVWCT      (SEQ ID NO: 29)

2) DCAYTNGNLVWCT      (SEQ ID NO: 31)

3) DCSYTNGNLVWCT      (SEQ ID NO: 32)

4) DCTWTNGNLVWCT      (SEQ ID NO: 34)

5) DCTYHNGNLVWCT      (SEQ ID NO: 35)

6) DCTYRNGNLVWCT      (SEQ ID NO: 36)

7) DCTYSNGNLVWCT      (SEQ ID NO: 37)

8) DCTYTRGNLVWCT      (SEQ ID NO: 39)

9) DCTYTNGELVWCT      (SEQ ID NO: 40)

10) DCTYTNGRLVWCT     (SEQ ID NO: 41)

11) DCTYTNGDLVWCT,    (SEQ ID NO: 42)
    and

12) DCTYTNGNLIWCT.    (SEQ ID NO: 45)
```

[10] The peptide according to any of [1] to [9], wherein the peptide has a disulfide bond formed between two cysteine (C) residues.
[11] The peptide according to any of [1] to [10], wherein the peptide is linked to a tag.
[12] A fusion protein consisting of the peptide according to any of [1] to [11] and a protein which is linked to the peptide.
[13] An immobilized peptide, wherein the immobilized peptide is the peptide according to any of [1] to [11] bound to a solid phase.
[14] A nucleic acid encoding the peptide according to any of [1] to [11].
[15] A method for purifying IgG, comprising binding the peptide according to any of [1] to [11] or the immobilized peptide according to [13] to IgG and collecting IgG by releasing the bound IgG.
[16] A method for detecting IgG, comprising binding IgG in a sample to the peptide according to any of [1] to [11] or the immobilized peptide according to [13] and detecting the bound IgG.
[17] A kit for analyzing or purifying human IgG, comprising at least one of the peptide according to any of [1] to [11] or the immobilized peptide according to [13].
[18] An IgG separation column, comprising the immobilized peptide according to [13].
[19] The peptide according to [1], comprising an amino acid sequence consisting of 13 to 17 amino acid residues, the peptide being capable of binding to human IgG, wherein the amino acid sequence is represented by the following formula I':

(X$_{1-3}$)-C-(X$_1$)-Y-H-R-G-N-L-V-W-C-(X$_{1-3}$)  (I')

wherein X each independently represents any amino acid residue except cysteine,
C represents a cysteine residue,
Y represents a tyrosine residue,
H represents a histidine residue,
R represents an arginine residue,
G represents a glycine residue,
N represents an asparagine residue,
L represents a leucine residue,
V represents a valine residue, and
W represents a tryptophan residue.
[20] The peptide according to [1], comprising an amino acid sequence consisting of 13 to 17 amino acid residues, the peptide being capable of binding to human IgG, wherein the amino acid sequence is represented by the following formula I":

(X$_{1-3}$)-C-A-(X$_1$)-H-R-G-E-L-V-W-C-(X$_{1-3}$)  (I")

wherein X each independently represents any amino acid residue except cysteine,
C represents a cysteine residue,
A represents an alanine residue,
H represents a histidine residue,
R represents an arginine residue,
G represents a glycine residue,
E represents a glutamic acid residue,
L represents a leucine residue,
V represents a valine residue, and
W represents a tryptophan residue.

The present specification encompasses the contents described in the specification and/or drawings of JP Patent Application (shutsugan) No. 2011-182539, to which the present application claims priority.

Advantageous Effects of Invention

The human IgG-binding peptide of the present invention is advantageous in that it can bind to human IgG more selectively than to IgA, IgM, and IgE, meaning that it can selectively separate IgG from, for example, human serum.

BRIEF DESCRIPTION OF DRAWINGS

FIG. 2 (A) shows the sequence of Lib-A and (B) shows the sequences of the peptides obtained from Lib-A.

FIG. 3 shows the sequence of Lib-B.

FIG. 4 shows the sequence of Lib-C.

FIG. 6 shows the sequence of Lib-D.

FIG. 7 shows the frequency of appearance of amino acids observed at respective positions based on the peptide sequence obtained from Lib-D.

DESCRIPTION OF EMBODIMENTS

Figure 1:
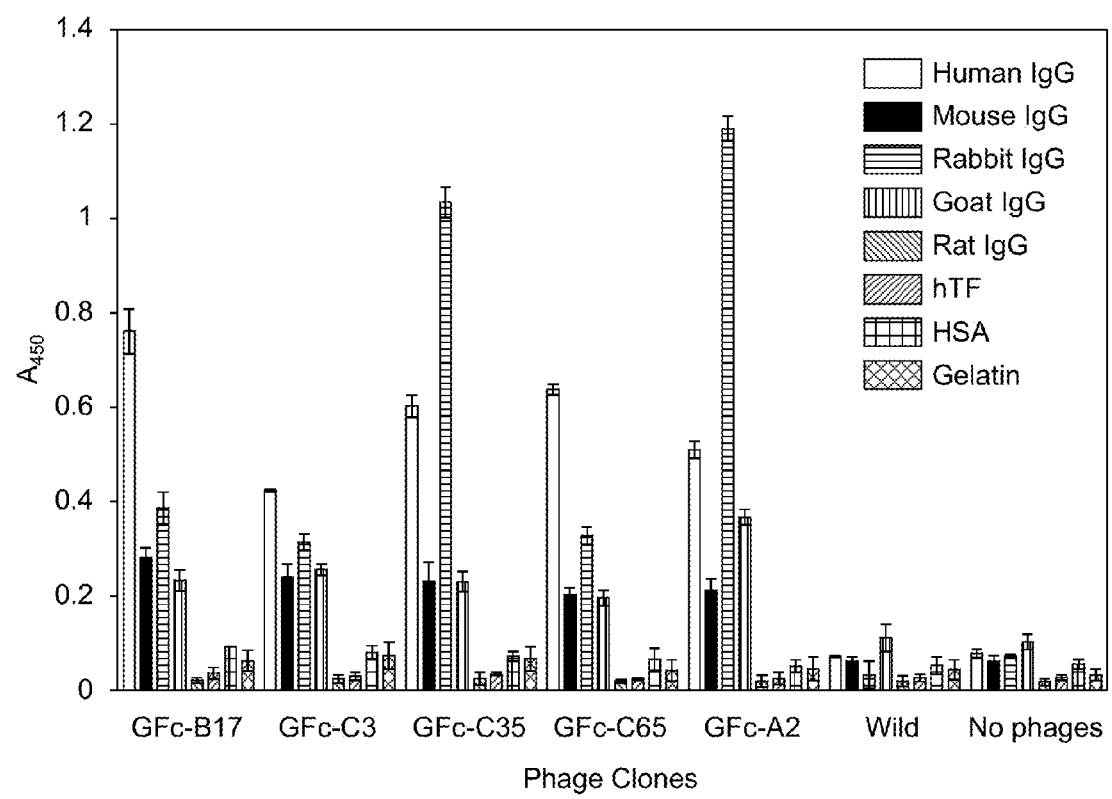
FIG. 1 shows the binding specificity of human IgG-binding phage clones by ELISA.

The peptide specifically or selectively binding to human IgG found by the present inventors this time was isolated, by biopanning, from libraries that were newly designed and constructed with reference to a random peptide library containing one intramolecular disulfide bond constructed by a T7 phage display system (Sakamoto, K., Ito, Y., Hatanaka, T., Soni, P. B., Mori, T., and Sugimura, K. (2009). The Journal of biological chemistry 284 (15), 9986 to 9993). Two specific clones obtained this time were homologous to each other, sharing a common sequence. Synthetic peptides prepared by causing various substitutions or deletions in this sequence showed specificity for IgG. The residues in these peptides essential for IgG binding were identified, and the application of these peptides to an approach to affinity enhancement and to purification of IgG from human serum was made possible. The most compact form of the IgG-binding peptide of the present invention is as small as 13-residue-long, offering the promise of construction of a low-cost peptide-based IgG purification system.

Hereinbelow, the present invention will be further described in detail.

Specifically, the IgG-binding peptide according to the present invention, the methods for purifying and analyzing IgG using the peptide, and the kit for such purification of IgG or detection of IgG will be described.

(IgG-binding Peptide)

The peptide of the present invention was screened as a peptide specifically or selectively binding to human IgG from phage libraries containing a large number of random peptides.

Human IgG used in the present specification refers to IgG1, IgG2, IgG3, and IgG4.

That is, the peptide of the present invention comprises an amino acid sequence consisting of 13 to 17 amino acid residues and is capable of binding to human IgG, wherein the amino acid sequence is represented by, as a primary structure in a broad sense, the following formula I:

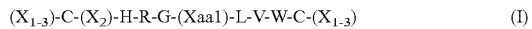

$$(X_{1-3})\text{-}C\text{-}(X_2)\text{-}H\text{-}R\text{-}G\text{-}(Xaa1)\text{-}L\text{-}V\text{-}W\text{-}C\text{-}(X_{1-3}) \quad (I)$$

wherein X each independently represents any amino acid residue except cysteine,

C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue, and
W represents a tryptophan residue.

In the above formula, the denotation of $X_{1-3}$ at the N terminus or C terminus indicates one to three consecutive amino acid residues X, each independently representing any amino acid residue except cysteine (C or Cys). Although the constituent amino acid residues of this moiety are the same or different, this moiety preferably consists of a sequence in which all three residues are not the same. Similarly, $X_2$ also indicates two consecutive amino acid residues X, each independently representing any amino acid residue except cysteine (C or Cys). Although the constituent amino acid residues of this moiety are the same or different, this moiety preferably consists of a sequence in which those two consecutive amino acid residues are different from each other.

Two cysteine residues in formula I can form a cyclic peptide via disulfide bonding. Normally, the peptide represented by formula I contains a disulfide bond.

Peptides represented by formulae I' and I", in which the amino acid residues X in the amino acid sequence of the peptide represented by formula I are further specified, are shown below.

That is, the peptide represented by formula I' comprises an amino acid sequence consisting of 13 to 17 amino acid residues and is capable of binding to human IgG, wherein the amino acid sequence is represented by:

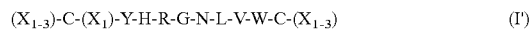

$$(X_{1-3})\text{-}C\text{-}(X_1)\text{-}Y\text{-}H\text{-}R\text{-}G\text{-}N\text{-}L\text{-}V\text{-}W\text{-}C\text{-}(X_{1-3}) \quad (I')$$

wherein X each independently represents any amino acid residue except cysteine,

C represents a cysteine residue,
Y represents a tyrosine residue,
H represents a histidine residue,
R represents an arginine residue,
G represents a glycine residue,
N represents an asparagine residue,
L represents a leucine residue,
V represents a valine residue, and
W represents a tryptophan residue.

The peptide represented by formula I" comprises an amino acid sequence consisting of 13 to 17 amino acid residues and is capable of binding to human IgG, wherein the amino acid sequence is represented by:

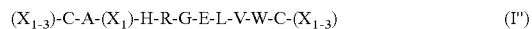

$$(X_{1-3})\text{-}C\text{-}A\text{-}(X_1)\text{-}H\text{-}R\text{-}G\text{-}E\text{-}L\text{-}V\text{-}W\text{-}C\text{-}(X_{1-3}) \quad (I'')$$

wherein X each independently represents any amino acid residue except cysteine,

C represents a cysteine residue,
A represents an alanine residue,
H represents a histidine residue,
R represents an arginine residue,
G represents a glycine residue,
E represents a glutamic acid residue,
L represents a leucine residue,
V represents a valine residue, and
W represents a tryptophan residue.

Further, a peptide represented by formula II, in which the amino acid residues X in the amino acid sequence of the peptide represented by formula I are further specified, is shown below.

That is, the peptide represented by formula II comprises an amino acid sequence consisting of 13 to 17 amino acid residues and is capable of binding to human IgG, wherein the amino acid sequence is represented by:

$$(X_{1-3})\text{-C-(Xaa2)-(Xaa3)-H-R-G-(Xaa1)-L-V-W-C-}(X_{1-3}) \quad (II)$$

wherein X each independently represents any amino acid residue except cysteine,
C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue,
W represents a tryptophan residue,
Xaa2 represents an alanine residue, a serine residue, or a threonine residue, and
Xaa3 represents a tyrosine residue or a tryptophan residue.

When the amino acid sequences of the peptides represented by the above formulae I', I", and II are 17 amino acid residues, the amino acid residues X at positions 1, 2, 16, and 17 from the N terminus may be deleted, and in such a case, the resulting peptides will be 13-amino acid-long.

In the present specification, the phrase "when . . . is 17 amino acid residues" is used for the sake of convenience to number 17 amino acid residues, which are the longest possible amino acid length, from amino acid position 1 to amino acid position 17 from the N terminus in order when the amino acid residues of a peptide are designated by amino acid numbers.

Furthermore, a peptide represented by formula III, in which the amino acid residues X in the amino acid sequence of the peptide represented by formula I are further specified, is shown below.

The peptide represented by formula III comprises an amino acid sequence consisting of 13 to 17 amino acid residues and is capable of binding to human IgG, wherein the amino acid sequence is represented by:

$$(X_{1-3})\text{-C-A-Y-H-R-G-E-L-V-W-C-}(X_{1-3}) \quad (III)$$

wherein X each independently represents any amino acid residue except cysteine,
C represents a cysteine residue,
A represents an alanine residue,
Y represents a tyrosine residue,
H represents a histidine residue,
R represents an arginine residue,
G represents a glycine residue,
E represents a glutamic acid residue,
L represents a leucine residue,
V represents a valine residue, and
W represents a tryptophan residue.

When the amino acid sequence of the peptide represented by the above formula III is 17 amino acid residues, the amino acid residues X at positions 1, 2, 16, and 17 from the N terminus may be deleted, and in such a case, the resulting peptide will be 13-amino acid-long.

Further, the amino acid residues other than cysteine (C) in the amino acid sequences of the peptides represented by respective formulae shown above, i.e., the amino acid residues at positions 1 to 3, 5, 6, and 15 to 17 from the N terminus when the peptide is 17 amino acid residues are each preferably selected from the following amino acid residues. Here, each alphabet in capital letter denotes the amino acid single letter code:

amino acid residue at position 1=S, G, F, or non-existent
amino acid residue at position 2=D, G, A, S, P, or non-existent
amino acid residue at position 3=S, D, T, N, E, or R,
amino acid residue at position 5=A or T,
amino acid residue at position 6=Y or W,
amino acid residue at position 15=S, T, or D,
amino acid residue at position 16=H, G, Y, T, N, D, F, or non-existent, and
amino acid residue at position 17=Y, F, H, M, or non-existent.
amino acid residue at position 5=A or T, and
amino acid residue at position 6=Y or W.

A peptide represented by formula IV, in which the amino acid residues X in the amino acid sequence of the peptide represented by formula I is further specified, is shown below.

The peptide represented by formula IV comprises an amino acid sequence consisting of 13 amino acid residues and is capable of binding to human IgG, wherein the amino acid sequence is represented by:

$$\text{D-C-(Xaa2)-(Xaa3)-H-R-G-(Xaa1)-L-V-W-C-T} \quad (IV)$$

wherein
D represents an aspartic acid residue,
C represents a cysteine residue,
H represents a histidine residue,
R represents an arginine residue,
G represents a glycine residue,
Xaa1 represents a glutamic acid residue or an asparagine residue,
L represents a leucine residue,
V represents a valine residue,
W represents a tryptophan residue,
T represents a threonine residue,
Xaa2 represents an alanine residue or a threonine residue, and
Xaa3 represents a tyrosine residue or a tryptophan residue.

Some specific examples of the peptide represented by formula I are listed in 1) to 17) below. Needless to say, the peptide is not limited to these examples. Any of the peptides shown below has strikingly higher binding specificity or binding selectively for human IgG than for other types of immunoglobulins:

```
                                      (SEQ ID NO: 47)
1) DCTYHRGNLVWCT (SEQ ID NO: 48)
2) DCAYHRGNLVWCT (SEQ ID NO: 50)
3) DCTYHRGELVWCT (SEQ ID NO: 52)
4) DCAYHRGELVWCT (SEQ ID NO: 53)
5) DCAWHRGELVWCT (SEQ ID NO: 55)
6) DCAYHRGELVWCT (SEQ ID NO: 56)
7) GPDCAYHRGELVWCTFH (SEQ ID NO: 57)
8) RCAYHRGELVWCS (SEQ ID NO: 58)
9) GPRCAYHRGELVWCSFH (SEQ ID NO: 100)
10) SPDCAYHRGELVWCTFH
```

```
                                       (SEQ ID NO: 101)
11) GDDCAYHRGELVWCTFH (SEQ ID NO: 102)
12) GPSCAYHRGELVWCTFH (SEQ ID NO: 103)
13) GPDCAYHRGELVWCSFH (SEQ ID NO: 104)
14) GPDCAYHRGELVWCTHH (SEQ ID NO: 105)
15) GPDCAYHRGELVWCTFY (SEQ ID NO: 106)
16) SPDCAYHRGELVWCTFY,
    and (SEQ ID NO: 107)
17) SDDCAYHRGELVWCTFY.
```

Further, the peptide of the present invention comprises an amino acid sequence consisting of 13 amino acid residues and is capable of binding to human IgG, wherein the amino acid sequence is represented by, as a primary structure in a broad sense, the following formula V:

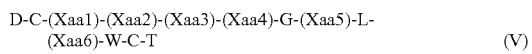

D-C-(Xaa1)-(Xaa2)-(Xaa3)-(Xaa4)-G-(Xaa5)-L-(Xaa6)-W-C-T    (V)

wherein
D represents an aspartic acid residue,
C represents a cysteine residue,
G represents a glycine residue,
L represents a leucine residue,
W represents a tryptophan residue,
T represents a threonine residue,
Xaa1 represents an alanine residue, a serine residue, or a threonine residue,
Xaa2 a tryptophan residue or a tyrosine residue,
Xaa3 a histidine residue, an arginine residue, a serine residue, or a threonine residue,
Xaa4 represents an asparagine residue or an arginine residue,
Xaa5 represents a glutamic acid residue, an asparagine residue, an arginine residue, or an aspartic acid residue, and
Xaa6 represents an isoleucine residue or a valine residue.

Two cysteine residues in formula V can form a cyclic peptide via disulfide bonding. Normally, the peptide represented by formula V contains a disulfide bond.

Some specific examples of the peptide represented by formula V are listed in 10) to 21) below. Needless to say, the peptide is not limited to these examples. Any of the peptides shown below has strikingly higher binding specificity or binding selectively for human IgG than for other types of immunoglobulins:

```
                                       (SEQ ID NO: 29)
10) DCTYTNGNLVWCT (SEQ ID NO: 31)
11) DCAYTNGNLVWCT (SEQ ID NO: 32)
12) DCSYTNGNLVWCT (SEQ ID NO: 34)
13) DCTWTNGNLVWCT (SEQ ID NO: 35)
14) DCTYHNGNLVWCT (SEQ ID NO: 36)
15) DCTYRNGNLVWCT (SEQ ID NO: 37)
16) DCTYSNGNLVWCT (SEQ ID NO: 39)
17) DCTYTRGNLVWCT (SEQ ID NO: 40)
18) DCTYTNGELVWCT (SEQ ID NO: 41)
19) DCTYTNGRLVWCT (SEQ ID NO: 42)
20) DCTYTNGDLVWCT,
    and (SEQ ID NO: 45)
21) DCTYTNGNLIWCT.
```

As described above, the peptides represented by the formulae shown above relating to the present invention are characterized in that two cysteine (C) residues are present separately from each other in respective amino acid sequences, wherein the two cysteine residues are arranged so that they can form a disulfide bond between them. A preferable peptide is a cyclic peptide formed by two cysteine residues via disulfide bonding, in which one or two arbitrary amino acid residues except cysteine may be present on the N terminal side and C terminal side of each cysteine residue. In the case that one or two arbitrary amino acid residues except cysteine are present on the N terminal side and C terminal side of each cysteine residue, each of the amino acid residues at positions 1 to 2 and 16 to 17 from the N terminus when the peptide is 17 amino acid residues is as exemplified above.

The binding affinity of the peptide of the present invention for human IgG is approximately 10 times, preferably approximately 50 times, and more preferably approximately 200 times as high as that for other human immunoglobulins (IgA, IgE, and IgM). The dissociation constant (Kd) for binding between the peptide of the present invention and human IgG can be determined by surface plasmon resonance spectral analysis (for example, by using BIACORE system), and for example, the dissociation constant is $1 \times 10^{-1}$ M to less than $1 \times 10^{-3}$ M, preferably less than $1 \times 10^{-4}$ M, more preferably less than $1 \times 10^{-5}$ M.

The peptide of the present invention can be produced by, for example, a peptide synthesis method such as conventional liquid phase peptide synthesis and solid phase peptide synthesis, and also by peptide synthesis by means of an automated peptide synthesizer (Kelley et al., Genetics Engineering Principles and Methods, Setlow, J. K. eds., Plenum Press NY. (1990) Vol. 12, pp. 1 to 19; Stewart et al., Solid-Phase Peptide Synthesis (1989) W. H. Freeman Co.; Houghten, Proc. Natl. Acad. Sci. USA (1985) 82: p. 5132, "Shin-seika-gakujikken kouza 1, tanpakushitsu IV (literal translation: New Biochemistry Experimentation Lecture 1 Protein IV) (1992), edited by The Japanese Biochemical Society, Tokyo Kagaku Dojin). Alternatively, the peptide can also be produced by means such as a gene recombination method using a nucleic acid encoding the peptide of the present invention and a phage display method. For example, the peptide of interest can be produced by incorporating DNA encoding the amino acid sequence of the peptide of the present invention into an expression vector, introducing the resulting vector into a host cell, and then culturing the host cell. The peptide thus produced can be collected or purified by a routine method, for example, chromatography such as gel filtration chromatography, ion exchange column chromatography, affinity chromatography, reverse phase column chromatography, and HPLC, ammonium sulphate fractionation, ultrafiltration, and immunoadsorption.

For peptide synthesis, amino acids are prepared, in each of which the functional groups other than the α-amino group and the α-carboxyl group, which are available for forming a bond, are protected, and the peptide bond formation reaction is allowed to proceed between the α-amino group and the α-carboxyl group of respective amino acids. Normally, the carboxyl group of an amino acid residue positioned at the C-terminus of a peptide is bound to a solid phase in advance via a suitable spacer or linker. The protective group at the amino terminus of the dipeptide obtained as above is selectively removed, followed by peptide bond formation between the resulting amino terminus and the α-carboxyl group of the next amino acid. The above operation is continuously carried out to produce a peptide having protected side groups, and finally, all of the protective groups are removed and the peptide is detached from the solid phase. The details of the kinds of protective groups, protection method, and peptide binding method are described in depth in the literature listed above.

Gene recombination method includes inserting DNA encoding the peptide of the present invention into a suitable expression vector, introducing the vector into a suitable host cell, culturing the cell, and collecting the peptide of interest from inside the cell or from the extracellular fluid. Examples of the vector include, but are not limited to, a vector such as a plasmid, a phage, a cosmid, a phagemid, and a virus. Examples of the plasmid vector include, but are not limited to, an E. coli-derived plasmid (such as pET22b(+), pBR322, pBR325, pUC118, pUC119, pUC18, pUC19, and pBluescript), a Bacillus subtilis-derived plasmid (such as pUB110 and pTP5), and a yeast-derived plasmid (such as YEp13 and YCp50). Examples of the phage vector include, but are not limited to, a T7 phage display vector (such as T7Select10-3b, T7Select1-1b, T7Select1-2a, T7Select1-2b, and T7Select1-2c (Novagen)) and a λ phage vector (such as Charon4A, Charon21A, EMBL3, EMBL4, λgt10, λgt11, λZAP, and λZAPII). Examples of the virus vector include, but are not limited to, an animal virus such as retrovirus, adenovirus, adeno-associated virus, vaccinia virus, and sendai virus, and an insect virus such as baculovirus. Examples of the cosmid vector include, but are not limited to, Lorist 6, Charomid 9-20, and Charomid 9-42. Examples of a known phagemid vector include, but are not limited to, pSKAN, pBluescript, pBK, and pComb3H. A vector can contain a regulatory sequence enabling the expression of the DNA of interest, a selection marker for selecting a vector containing the DNA of interest, and a multicloning site for inserting the DNA of interest. Such a regulatory sequence includes, for example, a promoter, an enhancer, a terminator, the S-D sequence or ribosome binding site, a replication origin, and a poly A site. Also, as the selection marker, for example, an ampicillin resistant gene, a neomycin resistant gene, a kanamycin resistant gene, and a dihydrofolate reductase gene can be used. The host cell into which the vector is to be introduced is, for example, a bacterium such as E. coli and Bacillus subtilis, a yeast cell, an insect cell, an animal cell (such as a mammalian cell), and a plant cell, and examples of transformation or transfection of these cells include calcium phosphate method, electroporation, lipofection, particle bombardment, and PEG method. The culture method of transformed cells is carried out in accordance with a common method used for culturing host organisms. For example, culture of microorganisms such as E. coli and yeast cells contains a carbon source, a nitrogen source, inorganic salts, and the like that can be utilized by the host microorganisms. In order to simplify the collection of the peptide of the present invention, it is preferable to allow the host cell to secrete the peptide produced by expression outside the cell. In order to carry out this, DNA encoding a peptide sequence enabling secretion of the peptide outside the cell is bound to the 5'-terminal side of DNA encoding the peptide of interest. A fusion peptide that has migrated to the cell membrane is cleaved by signal peptidase, resulting in secretion of the peptide of interest into the medium. Alternatively, it is also possible to collect the peptide of interest that has accumulated inside the cells. In this case, the cells are physically or chemically destroyed and the peptide of interest is collected by means of protein purification techniques.

In light of the above, the present invention further relates also to a nucleic acid encoding the peptide of the present invention. Here, the nucleic acid encompasses DNA or RNA (such as mRNA).

The peptide of the present invention may be labeled with a tag so as to enable the detection of IgG. Examples of the tag include, but are not limited to, a fluorescent dye, a chemiluminescent dye, an enzyme, a radioactive isotope, a fluorescent protein, and biotin. Examples of a preferable tag include a fluorescent dye such as fluorescein, a fluorescein derivative such as FITC, rhodamine, a rhodamine derivative such as tetramethylrhodamine, and Texas Red.

The peptide of the present invention may also be fused to an arbitrary protein. When the protein is a fluorescent protein such as green fluorescent protein (GFP) or an enzyme such as peroxidase, such a protein can be used as a tag. In this case, a fusion protein can be produced by linking the peptide of the present invention to the above protein via a suitable linker by means of a gene recombination method as needed. At this time, a fusion protein should be produced in such a way that the binding of the peptide of the present invention to human IgG is not impaired.

The peptide of the present invention can further be immobilized to a solid phase that can be loaded into an affinity column so that it can be used for, for example, separation, purification, and analysis of human IgG.

Examples of a preferable solid phase used for immobilization of the peptide include, but are not limited to, polystyrene, polyethylene, polypropylene, polyester, polyacrylonitrile, a styrene-butadiene copolymer, a (meth)acrylic acid ester polymer, fluorinated resin, silica g-el, cross-linked dextran, polysaccharide, polysaccharide such as agarose, glass, metal, a magnetic substance, and a combination of these substances. Such a solid phase may have an arbitrary form such as a tray, a ball, a fiber, a particle, a rod, a plate, a container, a cell, a microplate, a test tube, a film or a membrane, a gel, and a chip. Specific examples include a magnetic bead, a glass bead, a polystyrene bead, a sepharose bead, a silica gel bead, a polysaccharide bead, a polystyrene plate, a glass plate, and a polystyrene tube. Immobilization of the peptide of the present invention to these solid phases can be carried out by a method well known to those skilled in the art, for example, a physical adsorption method, a covalent binding method, and an ion binding method. Immobilization is preferably carried out by covalent binding, and the solid phase having a chemical functional group (such as a hydroxyl group, an amino group, and a N-hydroxysuccinimidyl group), preferably a chemical functional group having an alkylene chain of approximately 4 to 20 carbon atoms as a spacer on its surface is chemically reacted with the carboxyl terminus of the peptide to form an ester bond, an amide bond, or the like. A solid phase to which the peptide of the present invention is immobilized can be loaded in a column such as an affinity chromatography column and an HPLC column and used for detection, purification, or separation of human IgG.

(IgG Purification Method)

The present invention further provides a method for purifying IgG, comprising binding the above-described peptide or immobilized peptide of the present invention to IgG and collecting IgG by releasing the bound IgG.

A solid phase to which the peptide of the present invention is immobilized is loaded into a column such as an affinity chromatography column and an HPLC column, followed by equilibration with a suitable buffer. Subsequently, a human IgG-containing solution is applied at low temperature, i.e., room temperature to 0° C., preferably approximately 10° C. to 0° C., more preferably approximately 4° C. to bind human IgG to the peptide on the solid phase. For example, for separation of IgG in serum, the binding operation can be performed by applying an IgG-containing solution using a buffer having a pH in the neutral range, for example, pH 6.0 to 7.5. Elution can be carried out by passing a buffer having a pH in the acidic range, for example, pH 2 to 4 (for example, a 0.2 M glycine-HCl buffer containing 0.3 M NaCl, pH 3.5 to pH 2.5), through the column.

It can be determined whether IgG is collected by, for example, electrophoresis, followed by Western blot using an anti-human IgG antibody. As to the electrophoretic conditions, SDS-PAGE is performed using a 5 to 20% acrylamide gradient gel, and as to the conditions of Western blot, proteins after electrophoresis are transferred to a PVDF membrane, followed by blocking with skimmed milk and then detection using a goat anti-human IgG a chain antibody and a HRP-labeled mouse anti-goat IgG antibody.

The method of the present invention is useful for obtaining an IgG-rich fraction in the step of purifying IgG from an IgG-containing product that is produced by various methods. In light of this, it is preferable to use the method of the present invention for column chromatography such as affinity chromatography and HPLC. For purification of IgG, in addition to the aforementioned chromatography, routine protein purification techniques, for example, chromatography such as gel filtration chromatography, ion exchange column chromatography, and reverse phase column chromatography, ammonium sulphate fractionation, and ultrafiltration can be appropriately combined.

(IgG Analysis Method)

The present invention further provides a method for detecting IgG, comprising binding the above-described peptide or immobilized peptide of the present invention to IgG in a sample and detecting the bound IgG. At this point, detection includes a qualitative or quantitative analysis.

Detection of IgG can be carried out by binding a sample to a membrane, a polystyrene well plate, etc. while using a suitable buffer during the operation, bringing the labeled peptide of the present invention into contact with the bound sample, and after optional washing, qualifying or quantifying the level of labeling.

Alternatively, when an HPLC column to which the peptide of the present invention is immobilized as described above is used, detection of IgG can be carried out by injecting a sample containing human IgG into the column, passing through a binding buffer to bind human IgG to the peptide, recording protein detected at an absorbance of 280 nm or by fluorescence at 350 nm with excitation light of 280 nm, eluting IgG from the column using an elution buffer (for example, gradient elution using a 0.1 M glycine hydrochloride buffer containing 0.15 M NaCl, pH 2.5), and qualifying and quantifying IgG based on the peak appeared and the peak area.

(Kit and Column)

The present invention further provides a kit for analyzing (qualification, quantification, etc.) or purifying human IgG, comprising at least one of the above-described peptide or immobilized peptide of the present invention.

The individual peptides or immobilized peptides included in the kit of the present invention are separately stored in respective containers. Further, if necessary, an instruction manual illustrating the analysis and purification procedures of human IgG may be included in the kit. Further, the kit may also include a reagent and a buffer necessary for analysis as well as a column filled with the immobilized peptide, and the like.

The present invention further provides an IgG separation column, comprising the above-described immobilized peptide of the present invention.

The aforementioned IgG separation column is a column for separating IgG, and specifically, it encompasses a column such as a chromatography column and a high performance liquid chromatography (HPLC) column for analysis, purification, or fractionation of IgG. The column size is not particularly limited and can be varied according to the intended use (i.e., for analysis, purification, or fractionation), the amount of a sample to be applied or injected, and so on. Also, the material of the column may be a substance that is normally used as a column such as metal, plastic, and glass.

The above-described column can be produced by densely filling a column with the immobilized peptide of the present invention (in the dry or wet state) produced in accordance with the above-described technique.

EXAMPLES

Hereinbelow, the present invention will be further specifically described with reference to Examples; however, the scope of the present invention is not limited by these Examples.

The following biopanning technique was used to isolate human IgG-specific phages from a random peptide library containing a cyclic structure formed by two Cys residues, which was constructed by the T7 phage display method.

That is, a $5 \times 10^{10}$ pfu T7 phage library (a mixture of equal quantities of $X_3CX_8CX_3$, $X_3CX_9CX_3$, and $X_3CX_{10}CX_3$) solution in PBS containing 0.5% BSA and 0.1 µM type II IgG-binding peptide K6R (J. Biol. Chem. 284, 9986, 2009) was added to a 96-well microplate (Nunc, Maxisorp) coated with human IgG-Fc (from human plasma, Athens Research & Technology, Athens, Ga., USA) (1 µg/100 µl/well) that was blocked with 0.5% BSA, followed by reaction for one hour. After removal of the supernatant phage solution, the well was washed 10 times with PBS containing 0.1% Tween. A culture solution (300 µl) of *E. coli* BLT5615 (Novagen) was added and infection was carried out, and phages were propagated in 3 ml of a culture solution of *E. coli* at 37° C. and incubation was continued until bacteriolysis took place. Phages were collected from the culture solution after bacteriolysis by the phage precipitation method using polyethylene glycol in accordance with a conventional method. The phages thus obtained were dissolved in PBS and passed through a 0.45 µm filter, and then used for subsequent panning IgG-specific phages were concentrated by performing four rounds of panning, including the above panning round.

The binding specificity of the phages obtained after the fourth round of panning for a variety of IgG was examined by ELISA. As a result, as shown in FIG. 1, the phages showed binding activities not only for human IgG, but also for rabbit, goat, and mouse IgGs.

In light of the above results, the amino acid sequences were determined by analyzing the peptide motifs displayed by the phages obtained (Table 1).

TABLE 1

Comparison of peptide sequences
displayed by IgG-binging phages
obtained from a random peptide library

|  | 1****8-9*****17 | | |
|---|---|---|---|
| GFc-A2 | SFTCAYDRDGNLVWCTHS | SEQ ID NO: 1 | 1/30 |
| GFc-B17 | SSDCTYQR-GELVWCTHL | SEQ ID NO: 2 | 1/30 |
| GFc-C3 | PGECTKHM-GELVWCVSK | SEQ ID NO: 3 | 1/80 |
| GFc-C35 | GPDCTYTN-GNLVWCTFH | SEQ ID NO: 4 | 2/80 |
| GFc-C65 | KPRCSYLR-GQLVWCLHS | SEQ ID NO: 5 | 2/80 |
|  | *C***G*LVWC*** | | |

Amino acids of a peptide were numbered sequentially from 1 to 17 from the N-terminus based on the length of the peptide library of X₃CX₉CX₃.

With respect to GFc-C35, which exhibited a relatively high binding activity, peptides were synthesized and evaluated for their affinity by surface plasmon resonance (SPR) analysis. As a result, GFc-C35 was found to have low affinity with a Kd value of 14 µM, revealing that enhancement of affinity is necessary to use it as an affinity ligand.

In light of the above result, first of all, a library (library A: Lib-A, FIG. 2(A)) was constructed as follows: Focusing on the region sandwiched between two Cys residues, amino acids that were completely conserved in GFc-C35, which were Gly9, Leu11, Val12 and Trp13, and Thr15, were fixed, and the other regions were randomized using NNK-mixed nucleotides. From the peptide sequences obtained by biopanning, the characteristics of amino acids showing superiority in binding were evaluated (however, because almost no common features were observed with the position 1 of the amino acid sequences of the peptides obtained from the library, it was excluded from the construction of the above library). Using the library A constructed as above, biopanning was performed against human antibodies. The sequences of the peptides displayed by the phages thus obtained and the amino acids observed at respective amino acid positions are shown in FIG. 2 (B). At position 5, only Thr, Ser, and Ala with small side chains were observed, and at position 6, Trp is observed at the highest frequency or the position is occupied by Tyr and Phe having aromatic rings in the side chain. At position 7, His was observed at the highest frequency with a small number of Ser and Trp. Also, at position 8, Arg, Leu, and Met were observed at high frequency. Further, position 10 was occupied by hydrophilic amino acids, with the greatest number of Arg (FIG. 2).

The above results revealed the characteristics of side chains at respective positions important for IgG binding when Gly9, Leu11, Val12, Trp13, and Thr15 were fixed. In order to reconfirm the importance of conserved residues and screen for a peptide having an even stronger binding force, a library B: Lib-B was designed.

That is, as shown in FIG. 3, while maintaining the characteristics of the peptide sequences of the clones obtained from Lib-A, a library was constructed by introducing mutations also into the amino acids completely conserved in Table 1 (Leu11, Val12, Trp13, and Thr15) by introducing amino acids having similar side chains. However, Gly 9 was fixed since it was presumed to be important for maintaining the three-dimensional structure of the peptide. Amino acid residues outside the two Cys residues were excluded from the construction of the library. Instead, only the original peptide sequence of GFc-C35 (Asp3 and Thr15) was added). Using the library thus constructed, biopanning was carried out under stringent washing conditions, and the peptide sequences of clones exhibiting stronger binding activities by screening with ELISA were analyzed.

The sequences thus obtained are shown in Table 2.

TABLE 2

|  | 3 | 9 | | |
|---|---|---|---|---|
| 1-T3331 | DC SYRF | GELVW CT | SEQ ID NO: 6 |
| 2-T3338 | DC SYHF | GELVW CT | SEQ ID NO: 7 |
| 3-T33313 | DC AFHL | GHLVW CT | SEQ ID NO: 8 |
| 4-T33314 | DC AFHR | GDLVW CT | SEQ ID NO: 9 |
| 5-T33315 | DC AFHF | GDLVW CT | SEQ ID NO: 10 |
| 6-T33320 | DC TYHF | GKLVW CT | SEQ ID NO: 11 |
| 7-T33324 | DC AFHL | GELVR CT | SEQ ID NO: 12 |
| 8-T33317 | DC TWKF | GDLIW CT | SEQ ID NO: 13 |
| 9-T33339 | DC AYHL | GQLVR CT | SEQ ID NO: 14 |
| 10-T33341 | DC SFHL | GDLVW CT | SEQ ID NO: 15 |
| 11-T32213 | DC SYHL | GDYVW CT | SEQ ID NO: 16 |
| 12-T32222 | DC SWHM | GQLIW CT | SEQ ID NO: 17 |
|  | AYHF | DLVW | |
|  | SF L | E | |
|  | TW | | |

As a result, at position 5, Ala was most frequently observed, although it showed no marked superiority to Ser or Thr. At position 6, Tyr and Phe were dominant in place of Trp, which was significantly observed in Lib-A. At position 7, regardless of introduction of various amino acids in the library, His was predominant. At position 8, Phe and Leu were observed at high frequency in place of Arg and Leu in Lib-A. At position 10, while acidic amino acids Asp and Glu were observed at high frequency, a small number of positively-charged Lys, His, and Gln were also observed. Meanwhile, as anticipated from the sequences of the initially isolated clones, Leu11, Val12, and Trp13 were nearly completely conserved, with very few instances of substitution for Tyr at position 11, Ile at position 12, and Arg at position 13.

These frequently appearing amino acids are considered to reflect the contribution of the side chains of respective amino acids to IgG binding. The amino acids that were observed at high frequency in the peptide sequences of the clones obtained from the original library (library 0: Lib-0) and libraries A and B (Lib-A, B) are collectively shown with respect to respective positions in Table 3.

TABLE 3

Frequently appearing amino acids in the peptide sequences
of phages obtained from each library by panning

| | 5 | 6 | 7 | 8 | 9 | 10 | 11 | 12 | 13 | 15 | 16 |
|---|---|---|---|---|---|---|---|---|---|---|---|
| Lib 0 | | Y | | R | G | | L | V | W | T | H |
| Lib A | SAT | WFY | HSW | RLM | — | REN | — | — | — | — | |
| Lib B | AST | YFW | H | FL | — | DE | L | V | W | — | |
| Lib C | SA | WFY | H | L(R) | — | Q | ML | V(I) | W | TS | |

In the Table, "—" indicates fixed amino acids, each representing Gly9, Leu11, Val12, Trp13, and Thr15.

Based on the above information, a library was constructed by adding sequences to the outside of Cys on both sides and performing randomization (Lib-C, FIG. 4). This library was constructed so that the sequence inside Cys contained the amino acids frequently appearing in Libs-A and B, while the residues at the outside of Cys on both sides were either completely randomized with NNK-mixed nucleotides or contained amino acids similar to similar amino acids observed in Lib-0 or Lib-A. In constructing the library, Thr should have originally been put at position 6; however, because the number of amino acids would greatly increase by inclusion of Thr in nucleotide mixing, hydrophobic and/or aromatic amino acids were included in place of Thr. Also, although Ser, Arg, Trp, and the like should have originally been put at position 7, His was added because it was predominantly observed, and as a control therefor, Tyr and Gln were added.

Using the resulting library, clones with high binding properties were selected again by panning and the sequences were analyzed. The results are shown in Table 4.

TABLE 4

| GFc-C35 | GPDC TYTNG NLVWC TFH | SEQ ID NO: 4 |
|---|---|---|
| T6-1 | RGC SYHLG QLVWC TAV | SEQ ID NO: 18 |
| T6-2 | VKC SWHLG QMVWC TSN | SEQ ID NO: 19 |
| T6-7 | ANC SWHLG DMVWC STI | SEQ ID NO: 20 |
| T6-15 | VKC SWHLG QMVWC SNS | SEQ ID NO: 21 |
| T6-16 | VKC SWHLG QMVWC SNS | SEQ ID NO: 22 |
| T6-20 | LNC AFHRG RLVWC TDL | SEQ ID NO: 23 |
| T6-26 | SKC SFHLG QLIWC S | SEQ ID NO: 24 |

TABLE 4-continued

| T6-33 | TRC SYHLG EMVWC APS | SEQ ID NO: 25 |
|---|---|---|
| T6-41 | LNC AFHRG RLVWC TDL | SEQ ID NO: 26 |
| T6-43 | VGC AYHLG NMVWC TSF | SEQ ID NO: 27 |
|  | K   SW L   QM    T |  |
|  |     AY R    L    S |  |
|  |        F           |  |

As a result, although no characteristic amino acids appeared at positions 2 and 3 outside Cys on the N-terminal side, frequent appearance of Thr and Ser was observed at position 15 outside Cys on the C-terminal side. However, no characteristic amino acids were observed at positions 16 and 17. The internal sequences were almost consistent with the results of sequences obtained from Libs-0, A, and B (Table 3).

Next, the effect of the introduction of amino acids observed at high frequency at respective positions, which were considered to contribute to the enhancement of binding, was evaluated and studied using synthetic peptides.

In order to narrow down the amino acid region to be studied, a peptide in which one amino acid was deleted from each end of GFc-C35 (GFc-C35-2/16) and a peptide in which two amino acids were deleted from each end of CFc-C35 (GFc-C35-3/15) were synthesized. Among these peptides, based on the GFc-C35-3/15 synthetic peptide, the effect of the introduction of amino acid mutations on affinity was evaluated. That is, the contribution of each amino acid substitution to affinity was evaluated by synthesizing peptides substituted with frequently or occasionally observed amino acids obtained from the phage libraries and subjecting the resulting synthetic peptides to binding analysis. The results are shown in Table 5.

TABLE 5

Study of evaluation of affinity by amino acid substitutions in synthetic peptides

| Peptide | Sequence |  | Kd (µM) |
|---|---|---|---|
| GFc-C35 | GPDCTYTNGNLVWCTFH | SEQ ID NO: 4 | 14 |
| GFc-C35-2/16 | PDCTYTNGNLVWCTF | SEQ ID NO: 28 | 25 |
| GFc-C35-3/15 | DCTYTNGNLVWCT | SEQ ID NO: 29 | 130 |
| GFc-C35-3/15 (D3R) | RCTYTNGNLVWCT | SEQ ID NO: 30 | 69 |
| GFc-C35-3/15 (T5A) | DCAYTNGNLVWCT | SEQ ID NO: 31 | 61 |
| GFc-C35-3/15 (T5S) | DCSYTNGNLVWCT | SEQ ID NO: 32 | 120 |
| GFc-C35-3/15 (Y6F) | DCTFTNGNLVWCT | SEQ ID NO: 33 | 2100 |
| GFc-C35-3/15 (Y6W) | DCTWTNGNLVWCT | SEQ ID NO: 34 | 50 |
| GFc-C35-3/15 (T7H) | DCTYHNGNLVWCT | SEQ ID NO: 35 | 3 |
| GFc-C35-3/15 (T7R) | DCTYRNGNLVWCT | SEQ ID NO: 36 | 83 |
| GFc-C35-3/15 (T7S) | DCTYSNGNLVWCT | SEQ ID NO: 37 | 26 |
| GFc-C35-3/15 (N8L) | DCTYTLGNLVWCT | SEQ ID NO: 38 | 260 |
| GFc-C35-3/15 (N8R) | DCTYTRGNLVWCT | SEQ ID NO: 39 | 8 |
| GFc-C35-3/15 (N10E) | DCTYTNGELVWCT | SEQ ID NO: 40 | 26 |
| GFc-C35-3/15 (N10R) | DCTYTNGRLVWCT | SEQ ID NO: 41 | 42 |

TABLE 5-continued

Study of evaluation of affinity by amino acid substitutions in synthetic peptides

| Peptide | Sequence | | Kd (µM) |
|---|---|---|---|
| GFc-C35-3/15 (N10D) | DCTYTNGDLVWCT | SEQ ID NO: 42 | 80 |
| GFc-C35-3/15 (N10Q) | DCTYTNGQLVWCT | SEQ ID NO: 43 | 160 |
| GFc-C35-3/15 (L11M) | DCTYTNGNMVWCT | SEQ ID NO: 44 | 280 |
| GFc-C35-3/15 (V12I) | DCTYTNGNLIWCT | SEQ ID NO: 45 | 12 |
| GFc-C35-3/15 (T15S) | DCTYTNGNLVWCS | SEQ ID NO: 46 | 34 |

As a result of affinity analysis of a peptide lacking one amino acid at each end (GFc-C35-2/16) and a peptide lacking two amino acids at each end (GFc-C35-3/15), compared to the Kd value of GFc-C35 of 14 µM, the Kd values of GFc-C35-2/16 and GFc-C35-3/15 were increased to 25 µM and 130 µM, respectively, showing reduced affinity. These results revealed the contribution of the residues at both ends (positions 1, 2, 16, and 17) to binding.

As to Asp3, Arg was commonly observed in Lib-0 and Lib-C (Tables 1 and 4). As a result of comparing affinity between the substituted peptide (GFc-C35-3/15 (D3R)) and the original peptide (GFc-C35-3/15), an increase in affinity was observed.

As to Thr5, only Ala, Thr, and Ser were almost exclusively observed in Lib-A, none of which showed superiority to the others in the subsequent Libs-B and C (Table 3). As a result of comparing affinity among the two kinds of substituted peptides (GFc-C35-3/15 (T5A) and GFc-C35-3/15 (T5S)) and the original peptide (GFc-C35-3/15), a peptide substituted with Ala showed the highest affinity.

As to Tyr6, Trp, Tyr, and Phe were nearly equally observed in Libs-A and B; however, as a result of producing and evaluating peptides substituted with each of them, GFc-C35-3/15 (Y6F) showed greatly reduced affinity, while substitution for Trp (GFc-C35-3/15 (Y6W)) showed increased affinity.

As to Thr7, peptides substituted with each of His and Ser as obtained from Lib-A were produced and evaluated. Although both peptides showed greatly improved affinity, particularly, substitution for His showed markedly increased affinity (approximately 50-fold).

As to Asn8, substitution for Leu and Arg, which were observed at high frequency in Lib-0 and Libs-A and B, was performed. Substitution for Arg (GFc-C35-3/15 (N8R)) showed an approximately 18-fold decrease in Kd value, exhibiting greatly increased affinity. Meanwhile, substitution for Leu (GFc-C35-3/15 (N8L)) showed greatly degraded affinity.

As to Asn10, Arg and Glu, which are electrically opposed to each other, were observed at high frequency in Lib-A. Peptides into which these amino acids were introduced (GFc-C35-3/15 (N10R) and GFc-C35-3/15 (N10E)) both showed higher affinity than the original peptide (GFc-C35-3/15). These results suggest that electrically-charged residues could increase the binding activity. This is supposed by a finding that substitution of Asn10 for non-electrically-charged Gln (GFc-C35-3/15 (N10Q)) had almost equal affinity to the originally peptide, failing to achieve an affinity-enhancing effect. Meanwhile, although substitution of Asn10 for Asp (GFc-C35-3/15 (N10D)) also showed more or less improved affinity, the improvement of affinity was not as much as that achieved by a peptide substituted with Glu with a long side chain (GFc-C35-3/15 (N10E)). Accordingly, it was suggested that in order to improve affinity, the amino acid residue to be introduced had to have a side chain of a certain length.

As to Leu11, Leu is predominantly observed at position 11 in Lib-0 and Lib-B, manifesting itself as an important residue for binding; however, Met also appeared in Lib-C. In light of this, as a result of substitution of Leu11 for Met (GFc-C35-3/15(L11M)), a decrease in affinity was observed (approximately twice in terms of Kd value).

As to Val12, as a result of substitution for Ile as observed in Lib-C, the Kd value was decreased to approximately ¹⁄₁₀ of the original peptide, showing improved affinity.

As to Thr15, as a result of substitution for Ser, which appeared at high frequency in Lib-C, affinity increased compared to the original peptide (approximately ¼-fold in terms of Kd value).

Based on the above studies, peptides containing such combinations of amino acid substitutions that were predicted to contribute to the improvement of affinity were synthesized (Table 6).

TABLE 6

Improvement in the affinity of IgG-binding peptides by combinations of amino acid substitutions

| Peptide | Sequence | | Kd (µM) |
|---|---|---|---|
| GFc-C35-3/15 (T7H, N8R) | DCTYHRGNLVWCT | SEQ ID NO: 47 | 1.1 |
| GFc-C35-3/15 (T7H, N8R, T5A) | DCAYHRGNLVWCT | SEQ ID NO: 48 | 0.25 |
| GFc-C35-3/15 (T7H, N8R, Y6W) | DCTWHRGNLVWCT | SEQ ID NO: 49 | 2.0 |
| GFc-C35-3/15 (T7H, N8R, N10E) | DCTYHRGELVWCT | SEQ ID NO: 50 | 0.27 |
| GFc-C35-3/15 (T7H, N8R, V12I) | DCTYHRGNLIWCT | SEQ ID NO: 51 | 4.8 |
| GFc-C35-3/15 (T5A, T7H, N8R, N10E) | DCAYHRGELVWCT | SEQ ID NO: 52 | 0.054 |

TABLE 6-continued

Improvement in the affinity of IgG-binding peptides by combinations of amino acid substitutions

| Peptide | Sequence | | Kd (µM) |
|---|---|---|---|
| GFc-C35-3/15 (T5A, Y6W, T7H, N8R, N10E) | DCAWHRGELVWCT | SEQ ID NO: 53 | 0.26 |
| GFc-C35-3/15 (D3R, T5A, T7H, N8R, N10E, T15S) | RCAYHRGELVWCS | SEQ ID NO: 54 | 0.147 |

First of all, the most effective substitutions, Thr7His and Asn8Arg, were introduced (GFc-C35-3/15 (T7H, N8R)). As a result, the affinity-enhancing effect was noted with a reduced Kd value of 1.1 µM.

Further, into the above peptide (GFc-C35-3/15 (T7H, N8R)), each one of T5A, Y6W, N10E, and V12I, all of which were found to be effective in Table 5, was introduced. As a result, a peptide into which T5A or N10E was introduced, i.e., (GFc-C35-3/15 (T7H, N8R, T5A) or GFc-C35-3/15 (T7H, N8R, N10E)), showed an affinity-enhancing effect, whereas a peptide into which Y6W or V12I was introduced, i.e., (GFc-C35-3/15 (T7H, N8R, Y6W) or GFc-C35-3/15 (T7H, N8R, V12I)), exhibited reduced affinity. This suggests that even though individually advantageous modifications are added up, additivity properties cannot necessarily be held due to mutual compensation of effects or interaction.

Subsequently, the peptides exhibiting profound affinity-enhancing effects, i.e., GFc-C35-3/15 (T5A, T7H, N8R, N10E) and GFc-C35-3/15 (T5A, Y6W, T7H, N8R, N10E), were subjected to surface plasmon resonance (SPR) analysis.

Figure 5:
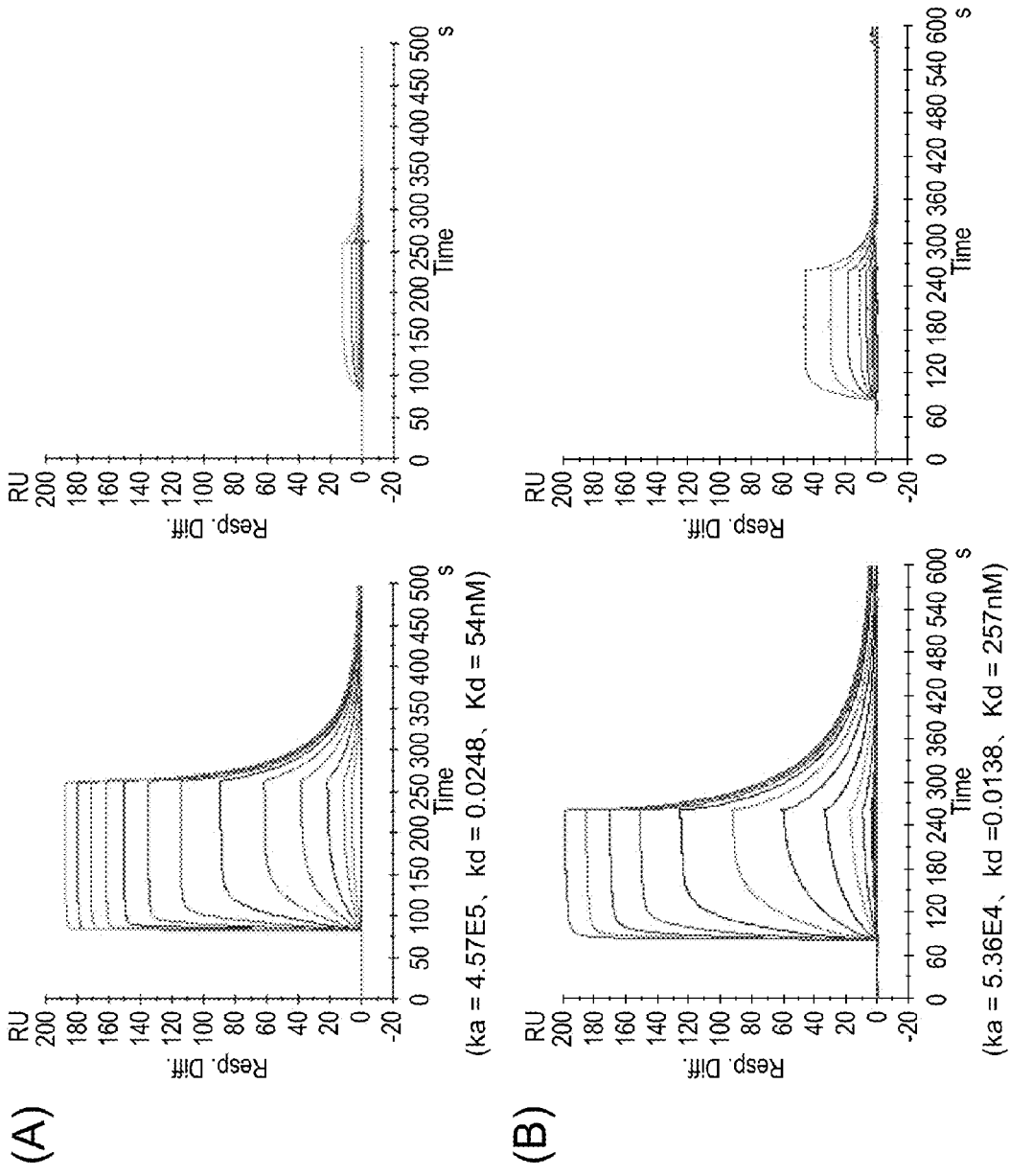
FIG. 5 shows the results of analysis of binding of (A) the GFc-C35-3/15 (T5A, T7H, N8R, N10E) peptide and (B) the GFc-C35-3/15 (T5A, Y6W, T7H, N8R, N10E) peptide to human IgG (left panels) and to human IgA (right panels) by surface plasmon.

The results are shown in FIG. 5.

The sensorgram analysis revealed that the affinity (Kd value) of GFc-C35-3/15 (T5A, T7H, N8R, N10E) was 54 nM, which was approximately 1/24 of the original peptide GFc-C35-3/15. Also, the association rate constant was as extremely fast as ka=4.6×10$^5$ M$^{-1}$S$^{-1}$, with a dissociation rate constant of kd=2.5×10$^{-2}$ S$^{-1}$.

The affinity (Kd value) of GFc-C35-3/15 (T5A, Y6W, T7H, N8R, N10E) was 257 nM, which was higher than that of the original peptide GFc-C35-3/15. The dissociation reaction rate constant kd value was 1.4×10$^{-2}$ S$^{-1}$, decreasing to half of GFc-C35-3/15 (T5A, T7H, N8R, N10E), showing that this modification contributed to an increase in affinity. On the other hand, the association rate constant ka drastically reduced to 5.4×10$^4$ M$^{-1}$S$^{-1}$ (1/8 or less), showing that the affinity of GFc-C35-3/15 (T5A, Y6W, T7H, N8R, N10E) decreased on the whole. As described above, the substitution of Y6W was shown to be very influential on both the Ka and Kd values.

The affinity of GFc-C35-3/15 (D3R, T5A, T7H, N8R, N10E, T15S) was 147 nM, which was higher than the original peptide GFc-C35-3/15. However, the affinity was lower than GFc-C35-3/15 (T5A, T7H, N8R, N10E).

From the above studies, GFc-C35-3/15 (T5A, T7H, N8R, N10E) was obtained, which had an approximately 2400-fold higher affinity than the original peptide GFc-C35-3/15. This peptide exhibiting the highest affinity will be referred to as C35A-3/15 hereinbelow.

From the results of Table 5, a peptide lacking one amino acid at each end of the GFc-C35 sequence (GFc-C35-2/16) and a peptide lacking two amino acids at each end of the GFc-C35 sequence (GFc-C35-3/15) had lower affinity than GFc-C35 in terms of their Kd values, revealing the contribution of residues at both ends (positions 1, 2, 16, and 17) to binding. In light of this, the contribution of two residues at both ends to binding was evaluated. With respect to C35A-3/15 exhibiting the highest affinity, a peptide (C35A) was synthesized by introducing Gly to position 1, Pro to position 2, Phe to position 16, and His to position 17, and the affinity was analyzed.

In order to confirm the effect of addition of these four amino acid residues, a peptide (C35A (D3R, T15S)) was synthesized also by introducing Gly to position 1, Pro to position 2, Phe to position 16, and His to position 17 of C35A-3/15 (D3R, T15S), and the affinity was analyzed. It is to be noted that C35A-3/15 (D3R, T15S) has the same sequence as GFc-C35-3/15 (D3R, T5A, T7H, N8R, N10E, T15S) shown in Table 6.

The results are shown in Table 7.

TABLE 7

| Peptide | Sequence | | Kd (µM) |
|---|---|---|---|
| C35A-3/15 | DCAYHRGELVWCT | SEQ ID NO: 55 | 0.054 |
| C35A | GPDCAYHRGELVWCTFH | SEQ ID NO: 56 | 0.009 |
| C35A-3/15 (D3R, T15S) | RCAYHRGELVWCS | SEQ ID NO: 57 | 0.147 |
| C35A(D3R, T15S) | GPRCAYHRGELVWCSFH | SEQ ID NO: 58 | 0.042 |

The peptide (C35A), in which Gly, Pro, Phe, and His were introduced to both ends of C35A-3/15, showed improved affinity compared to the original sequence (approximately 1/5 of the Kd value). Further, the peptide (C35A (D3R, T15S)), in which the same amino acids were introduced to both ends of C35A-3/15 (D3R, T15S), also showed improved affinity compared to the original sequence (approximately 1/3 of the Kd value).

Affinity was improved by introducing two residues at both ends (positions 1, 2, 16, and 17) in two kinds of peptides. This suggested that the sequences outside the Cys residues also contributed to the affinity for human IgG. That is, it was suggested that a sequence having higher affinity might be obtained by optimizing the sequences outside the Cys residues. In light of this, a library was constructed by fixing the sequence sandwiched between two Cys residues and randomizing the amino acids outside the Cys residues using XYZ-mixed nucleotides (Lib-D, FIG. 6), and from the peptide sequences obtained by biopanning, the characteristics of amino acids showing superiority in binding were evaluated.

That is, a 5×10$^{11}$ pfu T7 phage library (X$_3$CAYHRGELVWCX$_3$) solution was added to a 96-well microplate (Nunc, Maxisorp) coated with RNase (Ribonuclease A from bovine pancreas, SIGMA) (4 µg/400 µl/well) that was blocked with 0.5% BSA, followed by reaction for one hour (absorption step 1). The resulting supernatant was then added to a 96-well microplate (Nunc, Maxisorp) coated with HAS (Human serum albmin, SIGMA) (4 µg/400 µl/well)

that was blocked with 0.5% BSA, followed by reaction for one hour (absorption step 2). Subsequently, the resulting supernatant was transferred to a well coated with human IgG1 (monoclonal, Chugai Pharmaceutical Co., Ltd.) (1 µg/200 µl/well) that was blocked with 0.5% BSA, followed by reaction for one hour (binding step). After removal of the supernatant phage solution, the well was washed three times with PBS containing 0.1% Tween (washing step). A culture solution (200 µl) of E. coli BLT5403 (Novagen) was added and infection was carried out, and phages were propagated in 10 ml of a culture solution of E. coli at 37° C. and incubation was continued until bacteriolysis took place (propagation step). Phages were collected from the culture solution after bacteriolysis by the phage precipitation method using polyethylene glycol in accordance with a conventional method. The phages thus obtained were dissolved in PBS and used for subsequent panning IgG-specific phages were concentrated by performing seven rounds of panning, including the above panning round. However, from the second to seventh round of panning, the number of washes was increased at each step, resulting in a maximum of 30 washes. Also, no absorption step is performed during the sixth and seventh rounds of panning. After the seventh round of panning, single clones of phage were obtained and their binding specificity for human IgG was evaluated by ELISA. Among the evaluated phages, the peptide sequences displayed by the clones exhibiting high binding activities for human IgG were analyzed. The results are shown in Table 8.

TABLE 8

| Clone name | Sequence | | |
|---|---|---|---|
| 1-14 | NDTCAYHRGELVWCTYS | SEQ ID NO: | 59 |
| 1-15 | SDSCAYHRGELVWCDGY | SEQ ID NO: | 60 |
| 1-16 | VDSCAYHRGELVWCSNY | SEQ ID NO: | 61 |
| 1-23 | SAECAYHRGELVWCSVF | SEQ ID NO: | 62 |
| 1-27 | FNDCAYHRGELVWCSGY | SEQ ID NO: | 63 |
| 1-36 | HETCAYHRGELVWCDHH | SEQ ID NO: | 64 |
| 1-38 | SYECAYHRGELVWCSTY | SEQ ID NO: | 65 |
| 1-55 | SGNCAYHRGELVWCNFL | SEQ ID NO: | 66 |
| 2-1 | SGDCAYHRGELVWCSYH | SEQ ID NO: | 67 |
| 2-17 | LSSCAYHRGELVWCSHF | SEQ ID NO: | 68 |
| 2-18 | FSDCAYHRGELVWCGHF | SEQ ID NO: | 69 |
| 2-25 | GDPCAYHRGELVWCSNF | SEQ ID NO: | 70 |
| 2-33 | DVYCAYHRGELVWCNGD | SEQ ID NO: | 71 |
| 2-36 | GHSCAYHRGELVWCSHM | SEQ ID NO: | 72 |
| 2-38 | RGQCAYHRGELVWCSHY | SEQ ID NO: | 73 |
| 2-71 | EFNCAYHRGELVWCTDY | SEQ ID NO: | 74 |
| 2-72 | GRSCAYHRGELVWCSTF | SEQ ID NO: | 75 |
| 2-80 | TARCAYHRGELVWCEDM | SEQ ID NO: | 76 |

Based on the peptide sequences thus obtained, the frequency of appearance of amino acids observed at respective positions is shown in FIG. 7.

Ser was dominant at position 1 on the N-terminal side, followed by Gly, which was observed in the original sequence (C35A). At position 2, Asp and Gly dominantly appeared. At position 3, Ser dominantly appeared, followed by Asp, which was observed in the original sequence. At position 15 on the C-terminal side, the frequency of appearance of Ser was strikingly high. At position 16, His and Gly appeared at high frequency. At position 17, Tyr dominantly appeared, showing that the appearance of Tyr and Phe with aromatic rings was dominant. These results indicate that a peptide with higher affinity for human IgG may possibly be designed by introducing these amino acids to the sequences outside the two Cys residues.

Based on the above studies, the effect of the introduction of amino acids observed at high frequency at respective positions was evaluated and studied using synthetic peptides.

Based on the synthetic peptide C35A, peptides substituted with amino acids observed at high frequency in the aforementioned phage libraries were synthesized by introducing amino acid mutations, and in a similar manner to the above, their binding to human IgG was analyzed by surface plasmon resonance (SPR) analysis to evaluate the contribution of each amino acid substitution to affinity. The results are shown in the following Table 9.

TABLE 9

| Peptide | Sequence | | | Kd (µM) |
|---|---|---|---|---|
| C35A (G1S) | SPDCAYHRGELVWCTFH | SEQ ID NO: | 100 | 0.0093 |
| C35A (P2D) | GDDCAYHRGELVWCTFH | SEQ ID NO: | 101 | 0.0133 |
| C35A (D3S) | GPSCAYHRGELVWCTFH | SEQ ID NO: | 102 | 0.0285 |
| C35A (T15S) | GPDCAYHRGELVWCSFH | SEQ ID NO: | 103 | 0.0144 |
| C35A (F16H) | GPDCAYHRGELVWCTHH | SEQ ID NO: | 104 | 0.0114 |
| C35A (H17Y) | GPDCAYHRGELVWCTFY | SEQ ID NO: | 105 | 0.012 |
| C35A (G1S, H17Y) | SPDCAYHRGELVWCTFY | SEQ ID NO: | 106 | 0.011 |
| C35A (P2D, H17Y) | SDDCAYHRGELVWCTFY | SEQ ID NO: | 107 | 0.013 |

In order to confirm the utility of the resulting IgG-binding peptides, IgG purification from human serum was performed using an IgG-binding peptide-immobilized column. The IgG-binding peptide-immobilized column was produced by the following method.

To a HiTrap NHS-activated HP column (1 ml, GE Healthcare) equilibrated with 1 mM HCl (5 mL), 1 mL of a peptide solution (a solution of 4.0 mg N-terminally PEGylated C35A-3/15 ($NH_2$-PEG4-DCAYHRGELVWCT-$NH_2$) in 1.1 mL of a 0.05 M carbonate buffer (pH 8.3) (concentration: 1.5 mM)) was added and immobilization was carried out at room temperature for 30 minutes. Subsequently, the column was washed with 1 M Tris (1 mL), and blocking was carried out by adding 1 M Tris (2 mL) at room temperature for 30 minutes. The column was then washed three times with PBS (6 mL), and then once with PBS (1 mL). By the aforementioned operation, a peptide-immobilized column with an immobilization amount of 1.2 µmol was produced.

The resulting peptide-immobilized column (1.2 µmol) was employed in a Profinia protein purification system (BIO RAD), and a 5-fold diluted solution of human serum (1 mL) in PBS (5 mL) was applied to this peptide-immobilized column. After washing the column with PBS, stepwise elution was performed with 0.1 M glycine hydrochloride (pH 2.5). Elution of protein from the column was tracked by absorbance at 280 nm.

Figure 8:
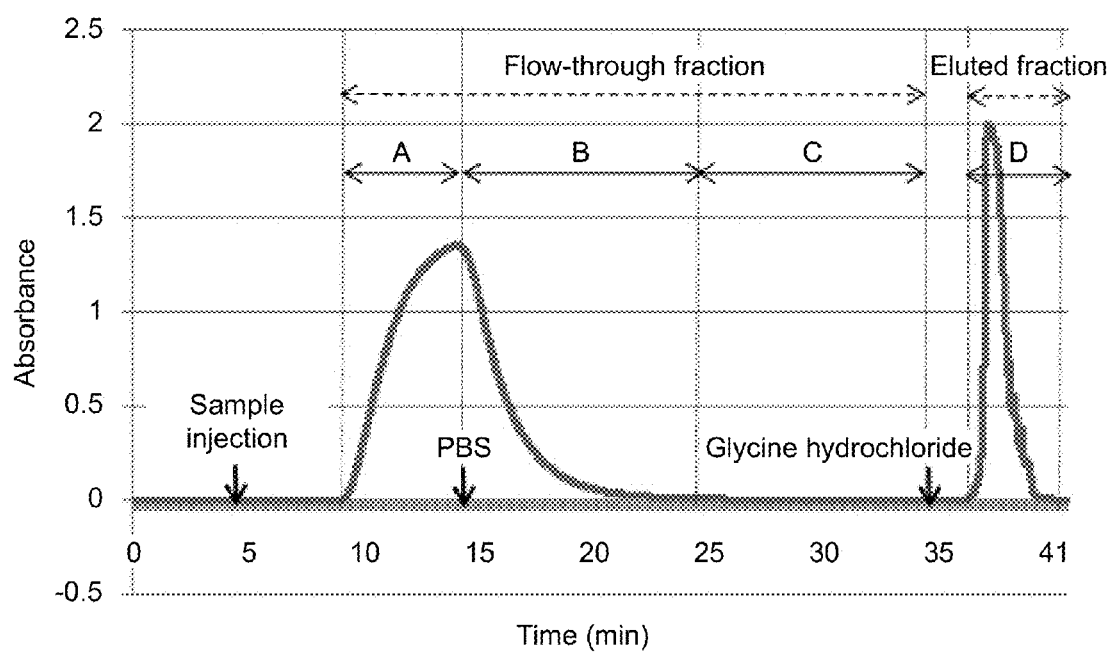
FIG. 8 shows the results of purification of IgG from human serum by an IgG-binding peptide-immobilized column.

The results are shown in FIG. 8.

From the measurement results of the absorbance of a solution of the eluted fraction (fraction D, 5 mL), the protein yield was confirmed to be 10.4 mg.

Figure 9:
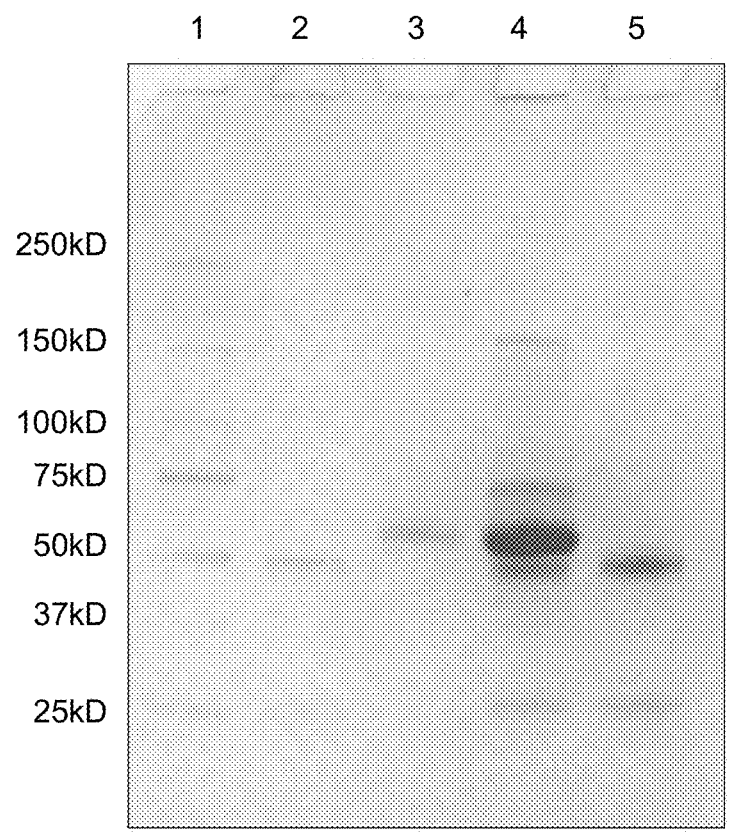
FIG. 9 shows the results of SDS-PAGE of the eluted fraction D purified from human serum by an IgG-binding peptide-immobilized column. Each lane represents the following sample. 1: Marker, 2: IgG, 3: HAS, 4: Serum, and 5: Eluted fraction D.

Confirmation of IgG in the eluted fraction D shown in FIG. 8 was carried out by SDS-PAGE (reducing treatment) in accordance with a conventionally known technique. That is, the eluted fraction D was reduced with 2-mercaptoethanol and then subjected to electrophoresis on a 4 to 20% polyacrylamide gradient gel (Mini-PROTEAN TGX g-el; BioRad), followed by staining with a Gelcode Blue Regent. As a result, clear bands were confirmed at around 25 kDa and 50 kDa, representing the light chain (L chain) and heavy chain (H chain) of IgG, respectively (lane 5 in FIG. 9). Lanes 1, 2, 3, and 4 each represent samples of a molecular weight marker, a reference human IgG preparation, HAS, and human serum, respectively.

The above results revealed that an IgG-binding peptide-immobilized column was applicable as an affinity column for purification of human IgG.

INDUSTRIAL APPLICABILITY

The present invention provides a peptide capable of specifically or selectively binding to human IgG, thereby being industrially useful for purification of IgG in the production of IgG as an antibody drug as well as for analysis of IgG.

All of the publications, patents, and patent applications cited in the present specification are herein incorporated by reference in their entirety.

The invention claimed is:

1. A peptide consisting of 13 to 17 amino acid residues in length comprising formula I:

(X$_{1-3}$)-C-A-Y-H-R-G-E-L-V-W-C-(X$_{1-3}$)     (I)(SEQ ID NO:108)

wherein X each independently represents any amino acid residue except cysteine,
C represents a cysteine residue,
A represents an alanine residue,
Y represents a tyrosine residue,
H represents a histidine residue,
R represents an arginine residue,
G represents a glycine residue,
E represents a glutamic acid residue,
L represents a leucine residue,
V represents a valine residue, and
W represents a tryptophan residue,
wherein the peptide is optionally linked to a tag, fused to a protein or immobilized on a solid phase. and wherein the peptide is not linked to, fused to or immobilized onto a T7 phage or T7 phage protein.

2. The peptide according to claim 1, wherein the amino acid residues at positions 1 to 3 and 15 to 17 of formula I are each as follows:
amino acid residue represented by X at position 1=S, G, F, or non-existent,
amino acid residue represented by X at position 2=D, G, A, S, P, or non-existent,
amino acid residue represented by X at position 3=S. D, T, N, E, or R,
amino acid residue represented by X at position 15=S, T, or D,
amino acid residue represented by X at position 16=H, G, Y, T, N, D, F, or non-existent, and
amino acid residue represented by X at position 17=Y, F, H, M, or non-existent.

3. The peptide according to claim 2, wherein the peptide is selected from the group consisting of 1) to 12):

```
                                    (SEQ ID NO: 55)
1) DCAYHRGELVWCT (SEQ ID NO: 56)
2) GPDCAYHRGETVWCTFH (SEQ ID NO: 57)
3) RCAYHRGELVWCS (SEQ ID NO: 58)
4) GPRCAYHRGELVWCSFH
```

-continued
```
                                    (SEQ ID NO: 100)
5) SPDCAYHRGELVWCTFH (SEQ ID NO: 101)
6) GDDCAYHRGELVWCTFH (SEQ ID NO: 102)
7) GPSCAYHRGELVWCTFH (SEQ ID NO: 103)
8) GPDCAYHRGELVWCSFH (SEQ ID NO: 104)
9) GPDCAYHRGELVWCTHH (SEQ ID NO: 105)
10) GPDCAYHRGELVWCTFY (SEQ ID NO: 106)
11) SPDCAYHRGELVWCTFY,
    and (SEQ ID NO: 107)
12) SDDCAYHRGELVWCTFY.
```

4. The peptide according to claim 1, wherein the peptide has a disulfide bond formed between two cysteine (C) residues.

5. The peptide according to claim 1, wherein the peptide is linked to a tag.

6. A fusion protein consisting of a peptide according to claim 1 and a protein which is linked to the peptide.

7. An immobilized peptide, wherein the immobilized peptide is a peptide according to claim 1 bound to a solid phase.

8. A nucleic acid encoding a peptide according to claim 1.

9. A method for purifying IgG, comprising binding a peptide according to claim 1 to IgG and collecting IgG by releasing the bound IgG.

10. A method for purifying IgG, comprising binding an immobilized peptide according to claim 7 to IgG and collecting IgG by releasing the bound IgG.

11. A method for detecting IgG, comprising binding IgG in a sample to a peptide according to claim 1 and detecting the bound IgG.

12. A method for detecting IgG, comprising binding IgG in a sample to an immobilized peptide according to claim 7 and detecting the bound IgG.

13. A kit for analyzing or purifying human IgG, comprising at least one of the peptides according to claim 1.

14. A kit for analyzing or purifying human IgG, comprising an immobilized peptide according to claim 7.

15. An IgG separation column, comprising an immobilized peptide according to claim 7.

* * * * *